US007220542B2

(12) United States Patent
Van Den Brink et al.

(10) Patent No.: US 7,220,542 B2
(45) Date of Patent: May 22, 2007

(54) EXPRESSION CLONING IN FILAMENTOUS FUNGI

(76) Inventors: Johannes Maarten Van Den Brink, Stockholmsgade 13-3 tv, Kobhavn-O, DK-2100 Denmark (NL); Gerardus Cornelis Maria Selten, Sterrenweg 81, 2651 HZ, Berkel en Rodenrijs (NL); Johannes Petrus Theodorus Wilhelmus Van Den Hombergh, Meentweg 77, 3454 AR De Meern, Meentweg (NL)

( * ) Notice: Subject to any disclaimer, the term of this patent is extended or adjusted under 35 U.S.C. 154(b) by 0 days.

(21) Appl. No.: 10/116,396

(22) Filed: Apr. 4, 2002

(65) Prior Publication Data

US 2004/0241647 A1    Dec. 2, 2004

Related U.S. Application Data

(63) Continuation of application No. 09/555,998, filed on Jul. 17, 2000, now abandoned.

(51) Int. Cl.
*C12Q 1/68* (2006.01)
(52) U.S. Cl. .................... 435/6; 435/484; 435/69.1; 435/463; 435/183
(58) Field of Classification Search .............. 435/6, 435/320.1, 325
See application file for complete search history.

(56) References Cited

U.S. PATENT DOCUMENTS 4,469,791 A    9/1984 Colson et al. .............. 435/253

FOREIGN PATENT DOCUMENTS

| EP | 0 238 023 A2 | 9/1987 |
|---|---|---|
| EP | 0 420 358 A1 | 4/1991 |
| EP | 0 429 628 B1 | 6/1991 |
| EP | 0 463 706 A1 | 1/1992 |
| EP | 0 635 574 A1 | 1/1995 |
| WO | WO 90/15860 | 12/1990 |
| WO | WO9015860 | * 12/1990 |
| WO | WO 91/00920 | 1/1991 |
| WO | WO 93/11249 | 6/1993 |
| WO | WO9311249 | * 6/1993 |
| WO | WO 94/14965 | 7/1994 |
| WO | WO 95/18219 | 7/1995 |
| WO | WO 95/34662 | 12/1995 |
| WO | WO 97/13853 | 4/1997 |
| WO | WO 98/45455 | 10/1998 |

OTHER PUBLICATIONS

Chaveroche et al. A rapid method for efficient gene replacement in the filamentous fungus *Aspergillus nidulans*. Nucl. Acids. Res. 28(22) 2000.*

Aleksenko et al. Autonomous Plasmid Replication in *Aspergillus nidulans*: AMA1 and MATE elements. Fungal Genetics and Biology. 21 373-387 1997.*

Vollmer et al., PNAS, vol. 83, 1986, pp. 4869-4873.*

Dalbøge, Henrik, "*Expression Cloning In Fungal Enzyme Genes; A Novel Approach For Efficient Isolation Of Enzymes Genes Of Industrial Relevance*", FEMS Microbiology Reviews, 21:2 pp. 29-42, 1997.

Berges, et al., "Cloning of an *Aspergillus niger* invertase gene by expression in *Trichoderma reesei*", Current Genetics, 1993, vol. 24, p. 53-59.

Aleksenko, et al., An "instant gene bank" method for gene cloning by mutant complementation, Mol Gen Genet. 1994, vol. 242, p. 467-471.

Yelton, et al., "A cosmid for selecting genes by complementation in *Aspergillus nidulans*: Selection of the developomentally regulated yA locus", Proc. Natl. Acad. Sci. USA 1985, vol. 82, p. 834-838.

Verdoes, et al., "Characterization of an efficient gene cloning strategy for *Aspergillus niger* based on an autonomously replicating plasmid: cloning of the nicB gene of A. niger", Gene, 1994, vol. 146, p. 159-165.

Fierro, et al., "Autonomously replicating plasmids carrying the AMA1 region in *Penicillium chrysogenum*", 1196, vol. 29, p. 482-489.

Aleksenko, et al., "Gene expression from replicating plasmids in *Aspergillus nidulans*", 1996, vol. 253, p. 242-246.

Cambareri, et al., "A simple and efficient system for targeting DNA to the am locus of *Neurospora crazza*", 1994, vol. 142, 219-224.

Miller, et al., "Direct and Indirect Gene Replacements in *Aspergillus nidulans*", 1985, vol. 5, p. 1714-1721.

Punt, et al., "Functional elements in the promoter region of the *Aspergillus nidulans* gpdA gene encoding glycer-aldehyde-3-phosphate dehydrogenase", 1990, vol. 93, p. 101-109.

Punt, et al., "A mini-promoter lacZ gene fusion for the analysis of fungal transcription control sequences", 1995, vol. 158, p. 119-125.

Johnstone, et al., "An autonomously replicating plasmid transforms *Aspergillus nidulans* at high frequency", Gene, 1991, vol. 98, p. 61-67.

Punt, et al., "A twin-reporter vector for simultaneous analysis of expression signals of divergently transcribed, contiguous genes in filanentous fungi", Gene, 1991, vol. 104, p. 119-122.

* cited by examiner

*Primary Examiner*—James Ketter
(74) *Attorney, Agent, or Firm*—McDonnell, Boehnen, Hulbert & Berghoff

(57) ABSTRACT

Methods are provided for isolation of DNA sequences encoding proteins with properties of interest by means of expression cloning in filamentous fungal host cells. The isolated DNA sequences are useful in processes for producing the proteins of interest.

13 Claims, 18 Drawing Sheets

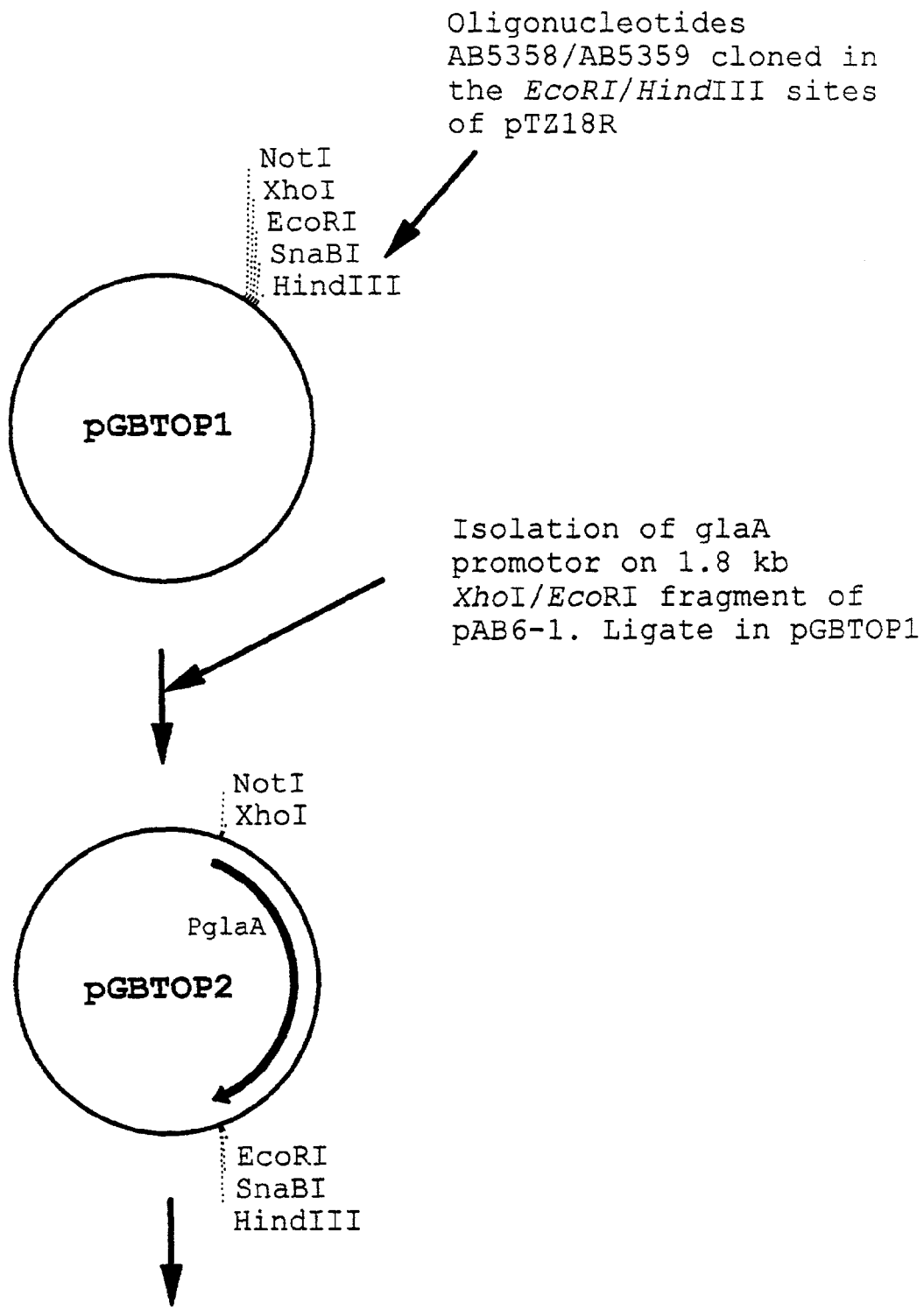

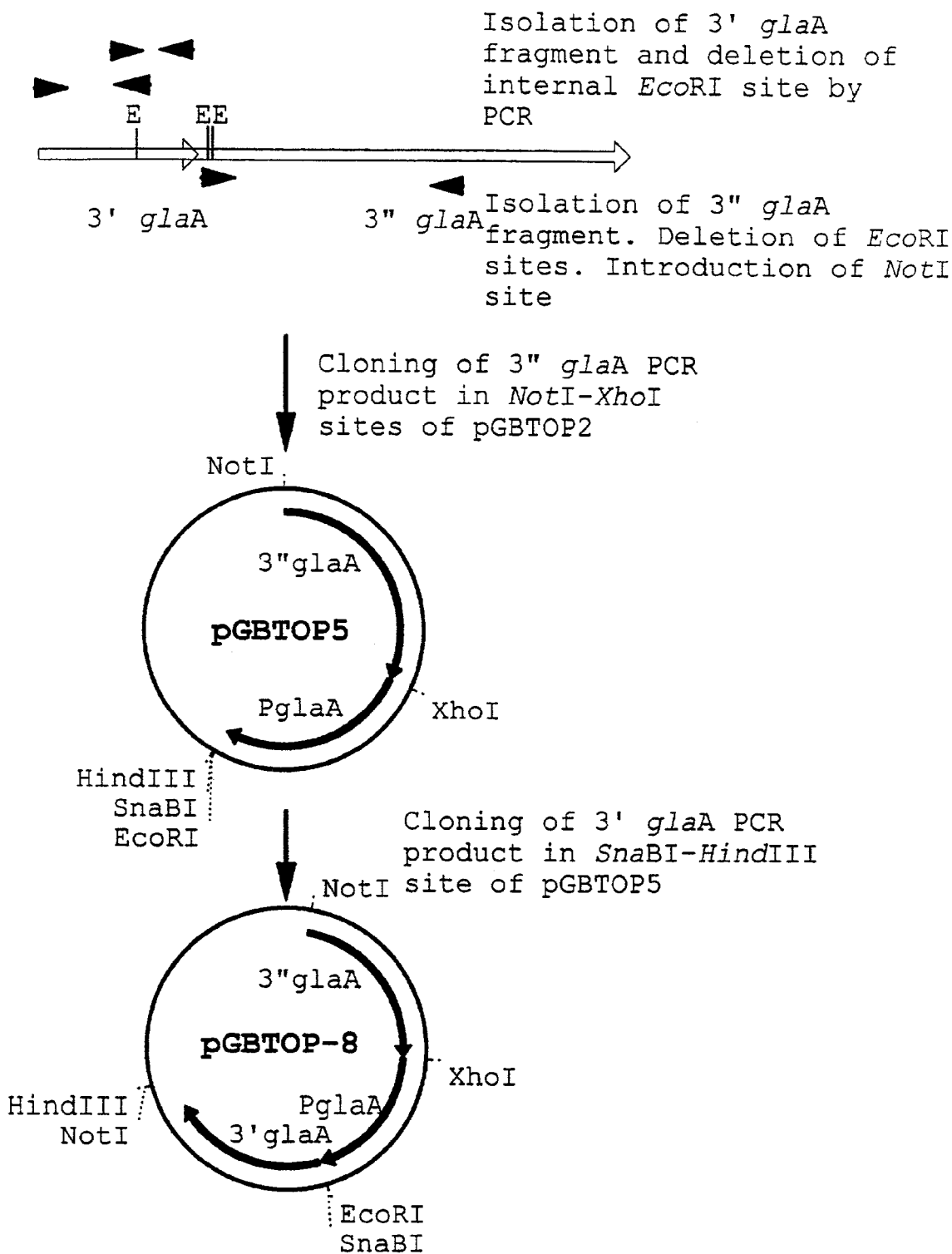
Figure 1, continued

Construction of pGBFin2

Fig. 2A, continued 1
Construction of pGBFin2
PCR on P*gpdA-amdS* fragment. Introduction of *XhoI* sites
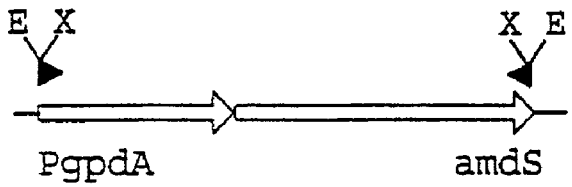
PgpdA            amdS
Digest PCR fragment with *EcoRI*. Clone in pTZ19R (pTZamdS-X1) Replace 0.5 kb kb *KpnI-ClaI* fragment of pTLamdS1 with *KpnI-ClaI* fragment from pTZamdS-X1
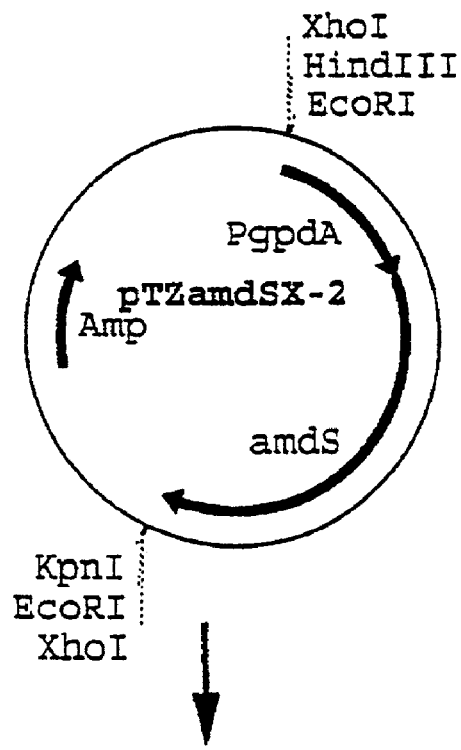

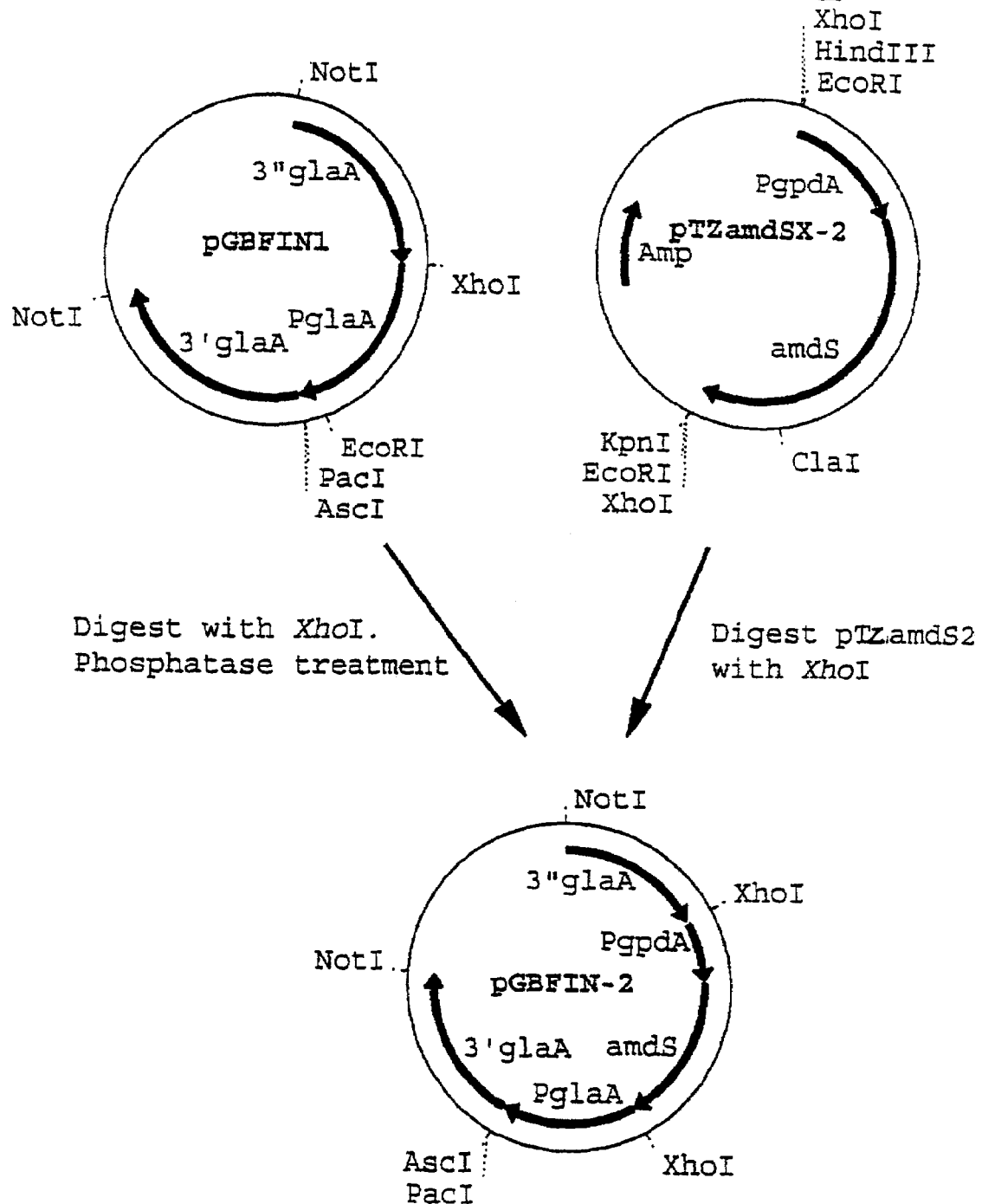
Fig. 2A, continued 2

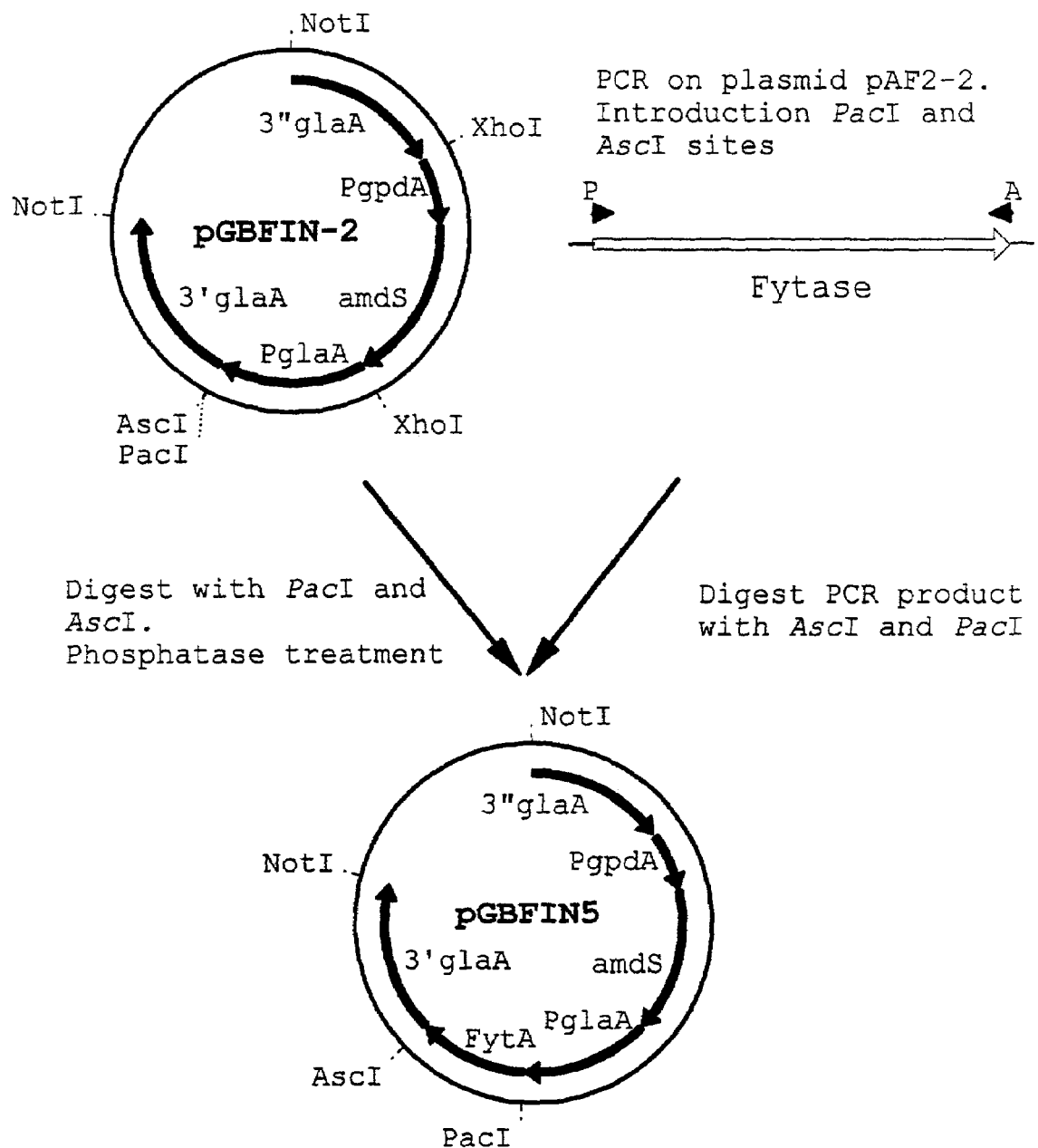

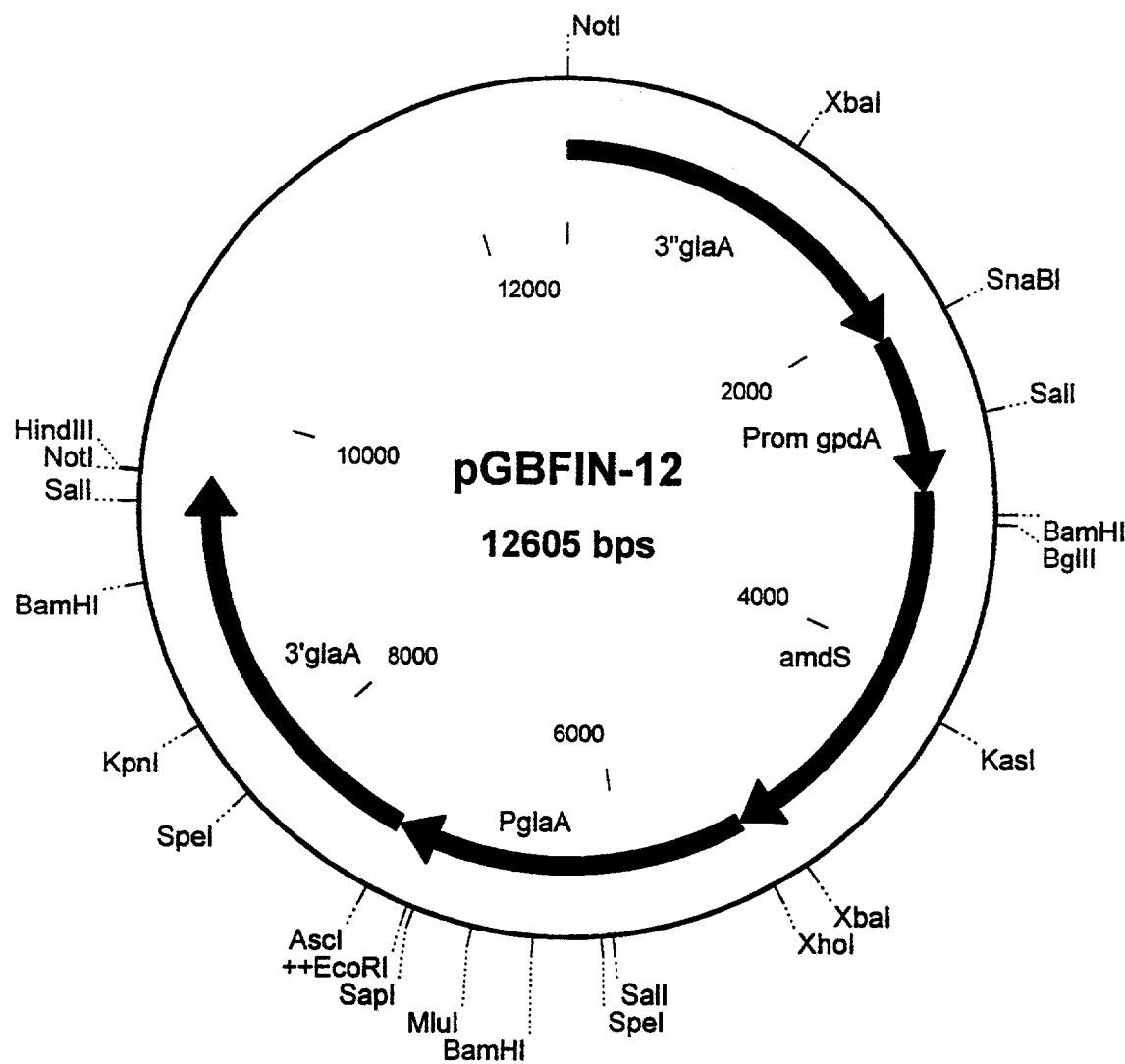
Figure 3: Physical map of pGBFin12 plasmid

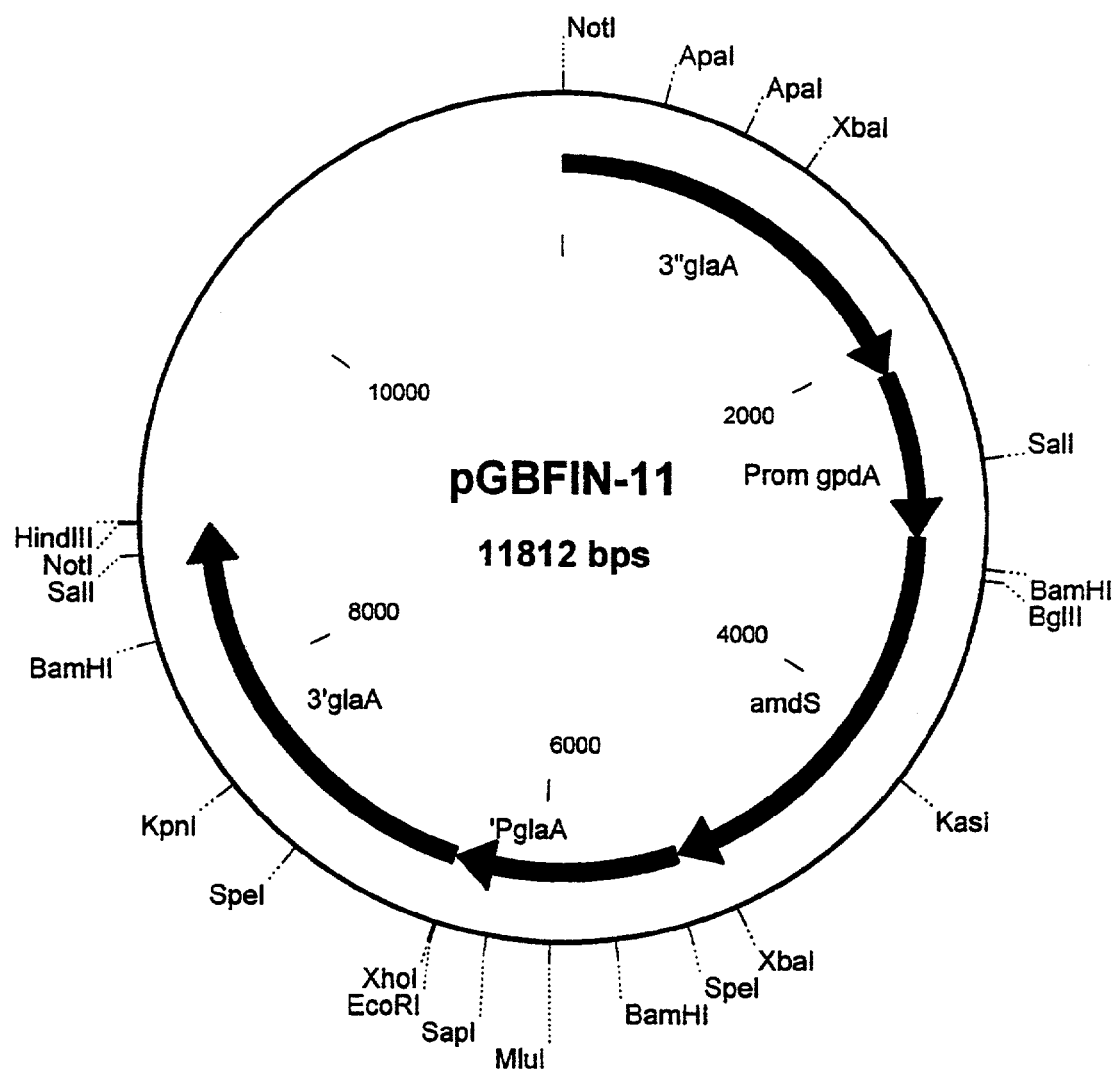
Figure 4: Physical map of pGBFin11 plasmid

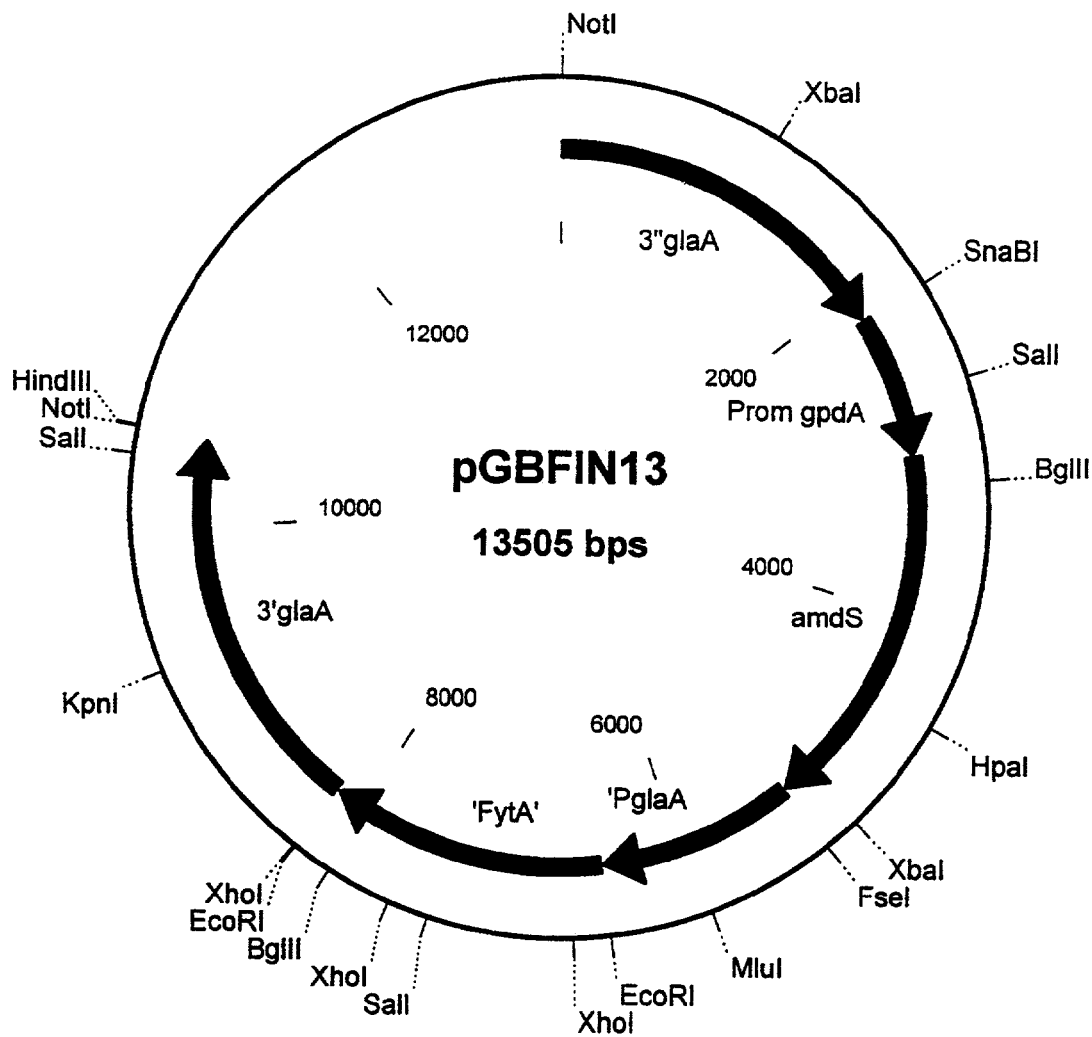
Figure 5: Physical map of pGBFin13 plasmid

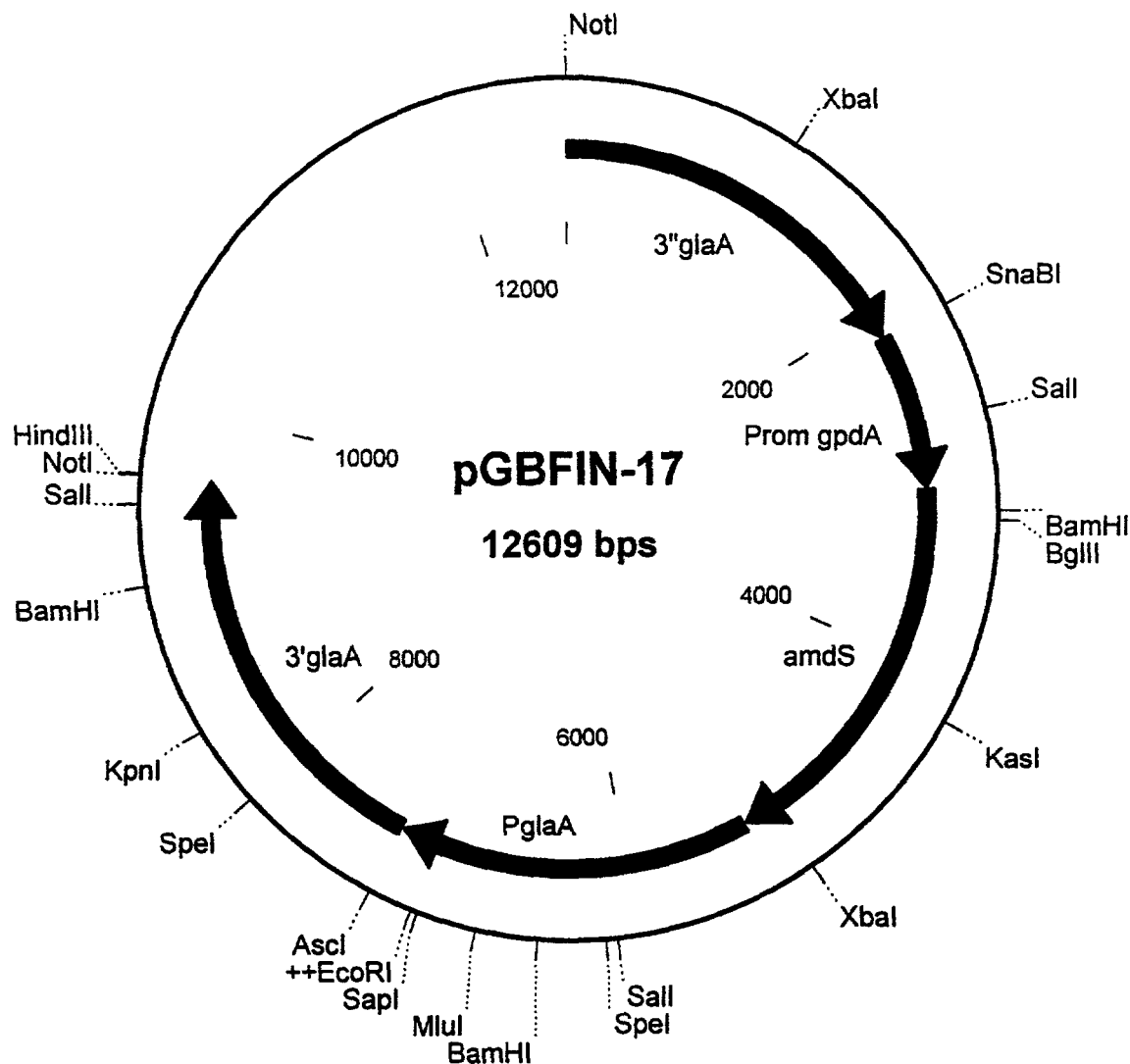
Figure 6: Physical map of pGBFin17 plasmid

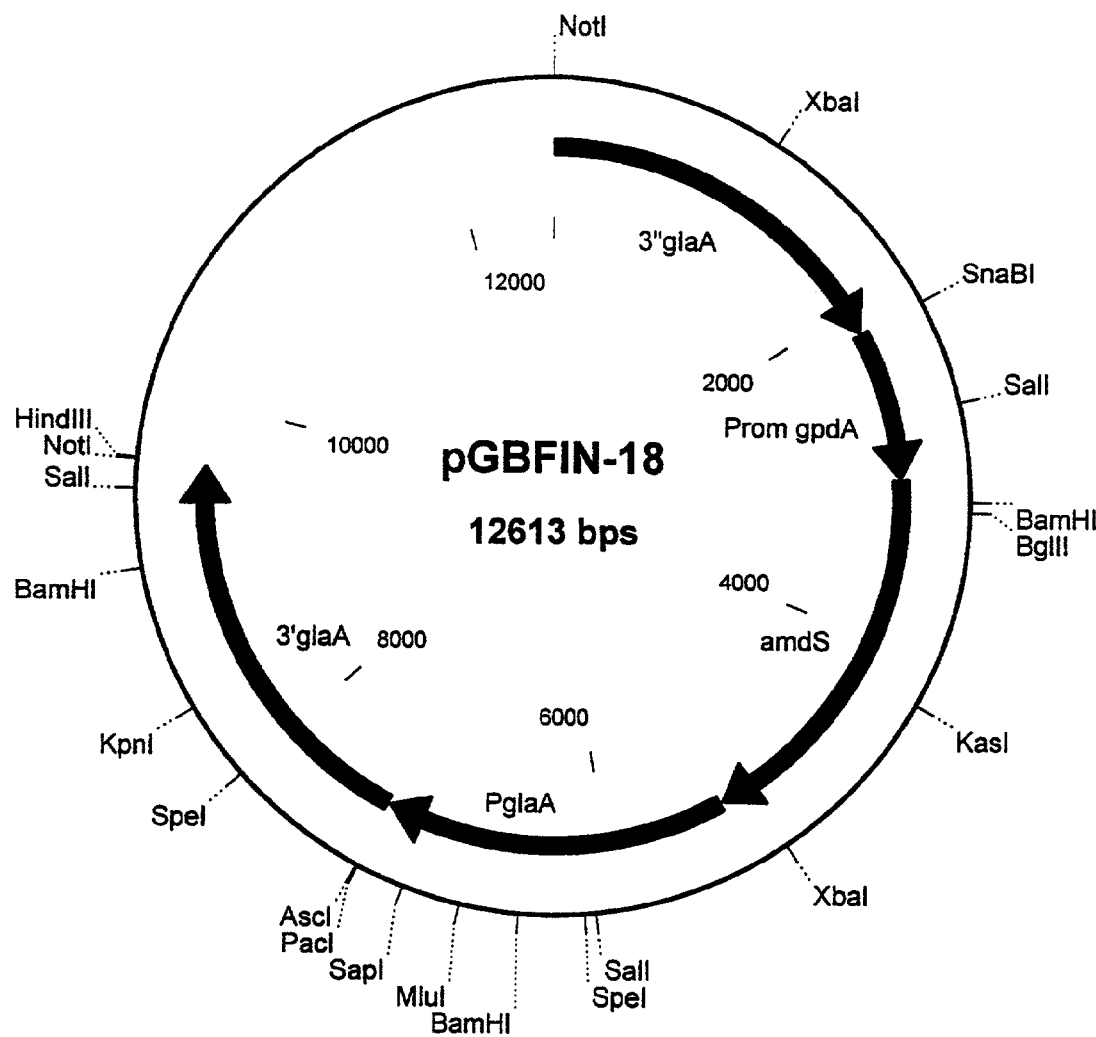
Figure 7: Physical map of pGBFin18 plasmid

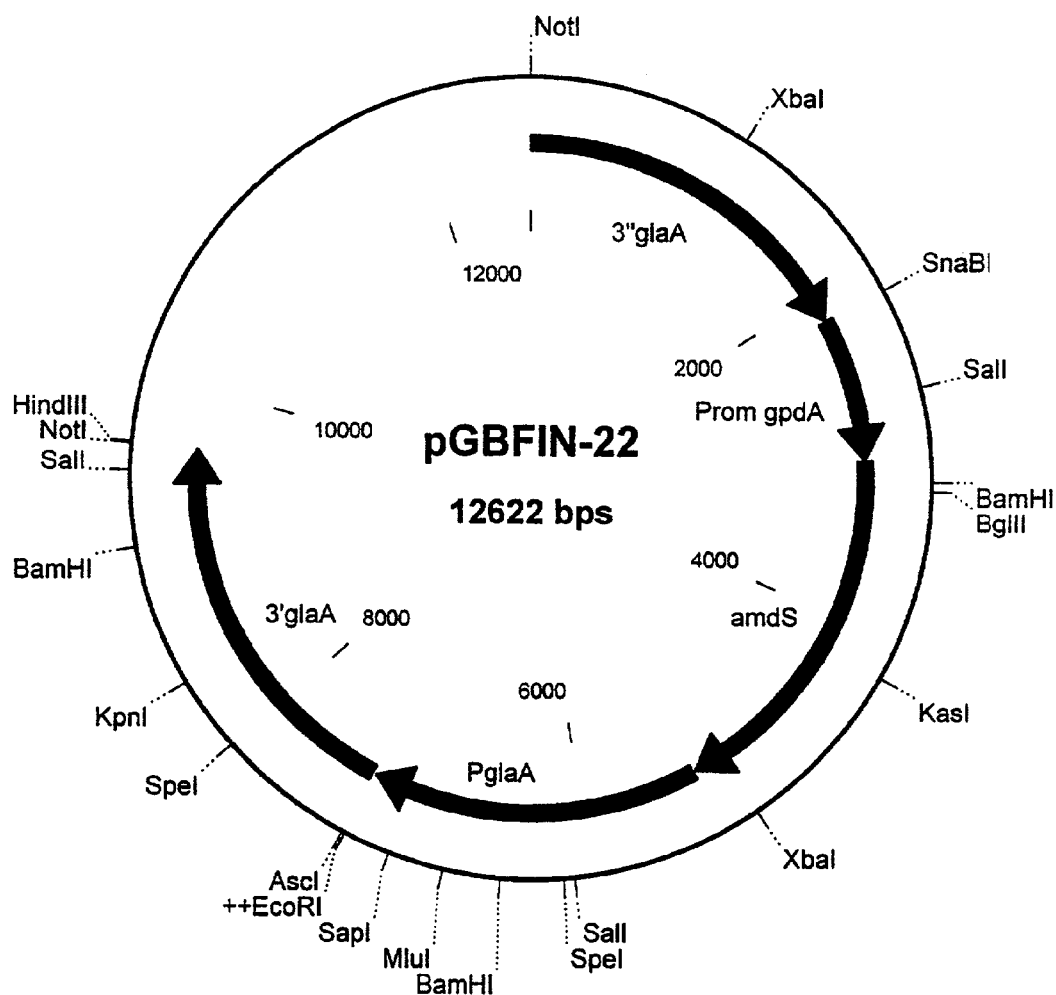
Figure 8: Physical map of pGBFin22 plasmid

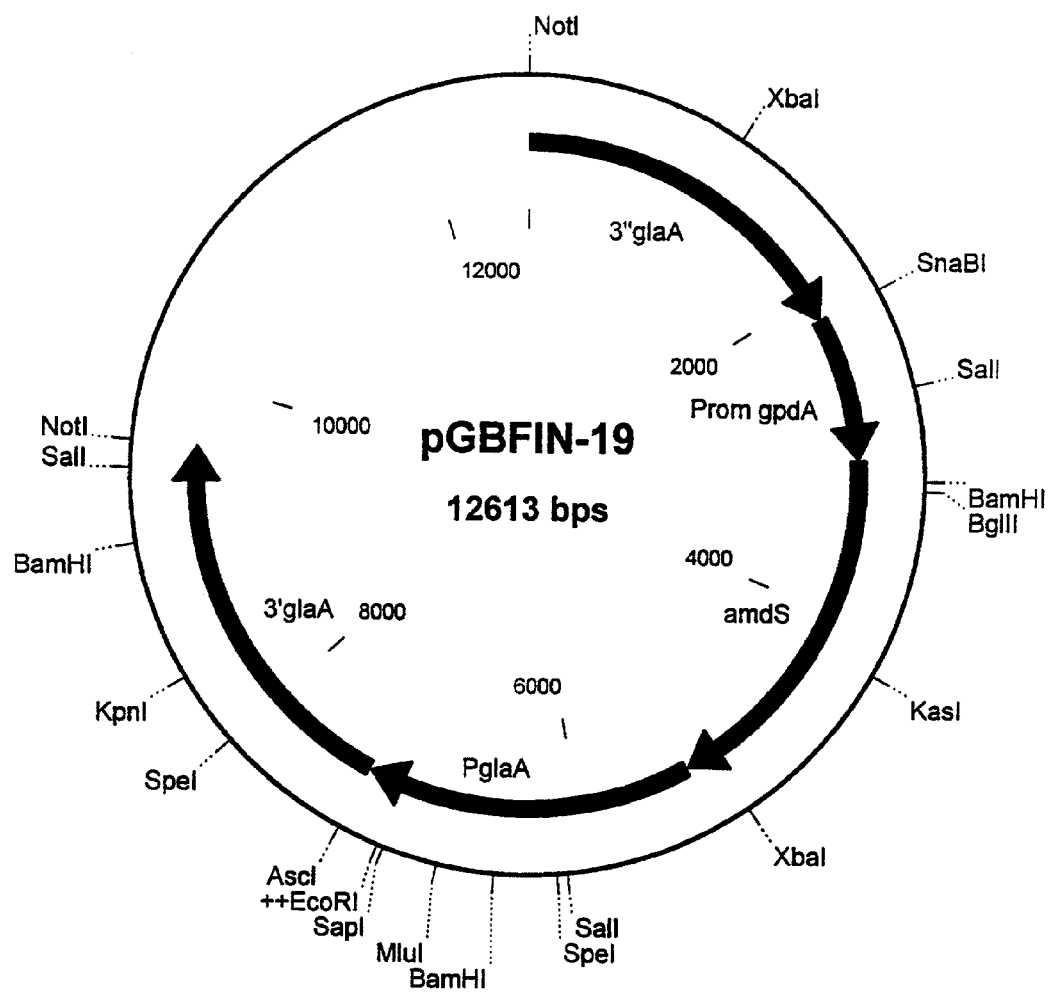
Figure 9: physical map of pGBFin19 plasmid

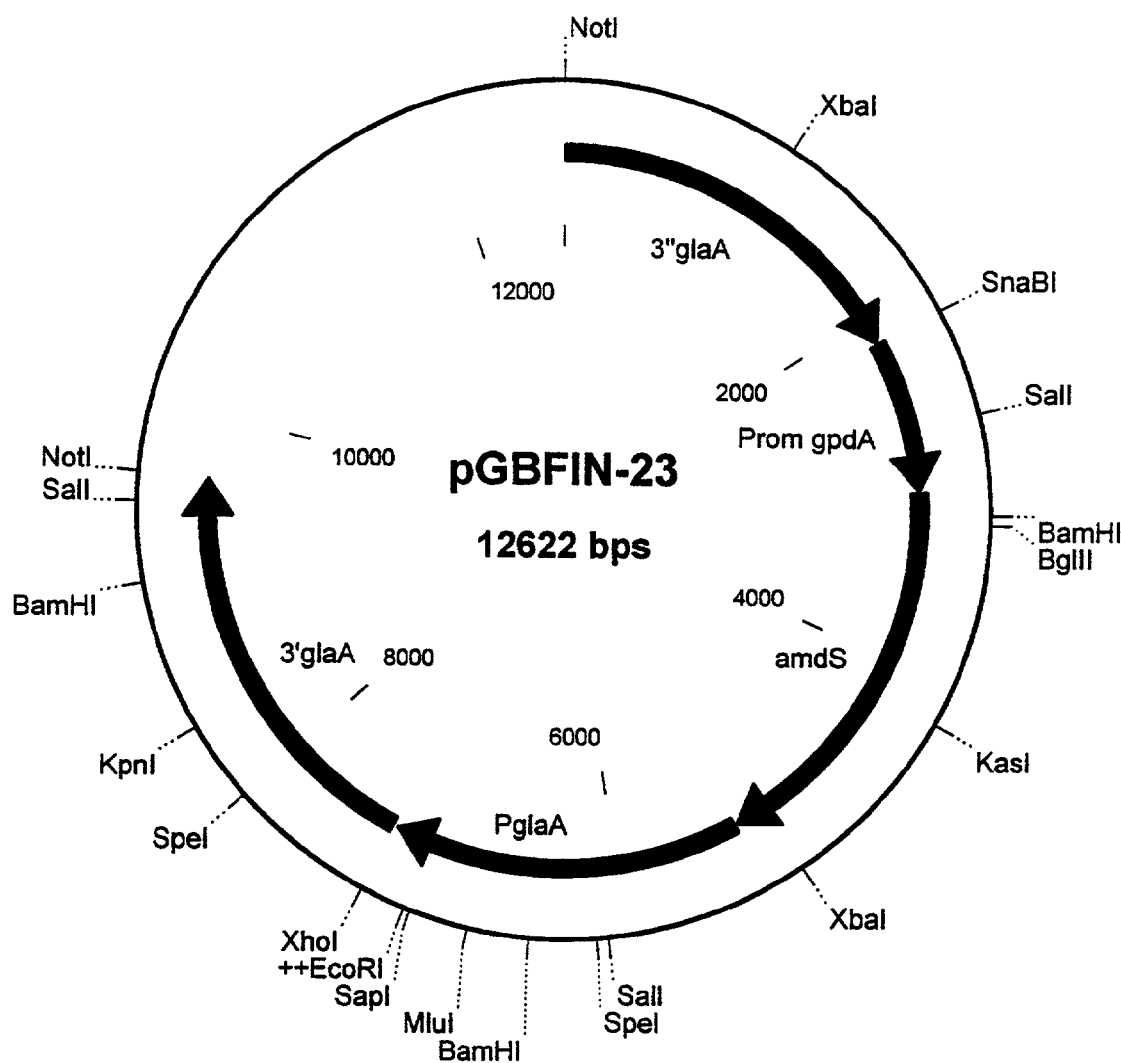
Figure 10: Physical map of pGBFin23 plasmid

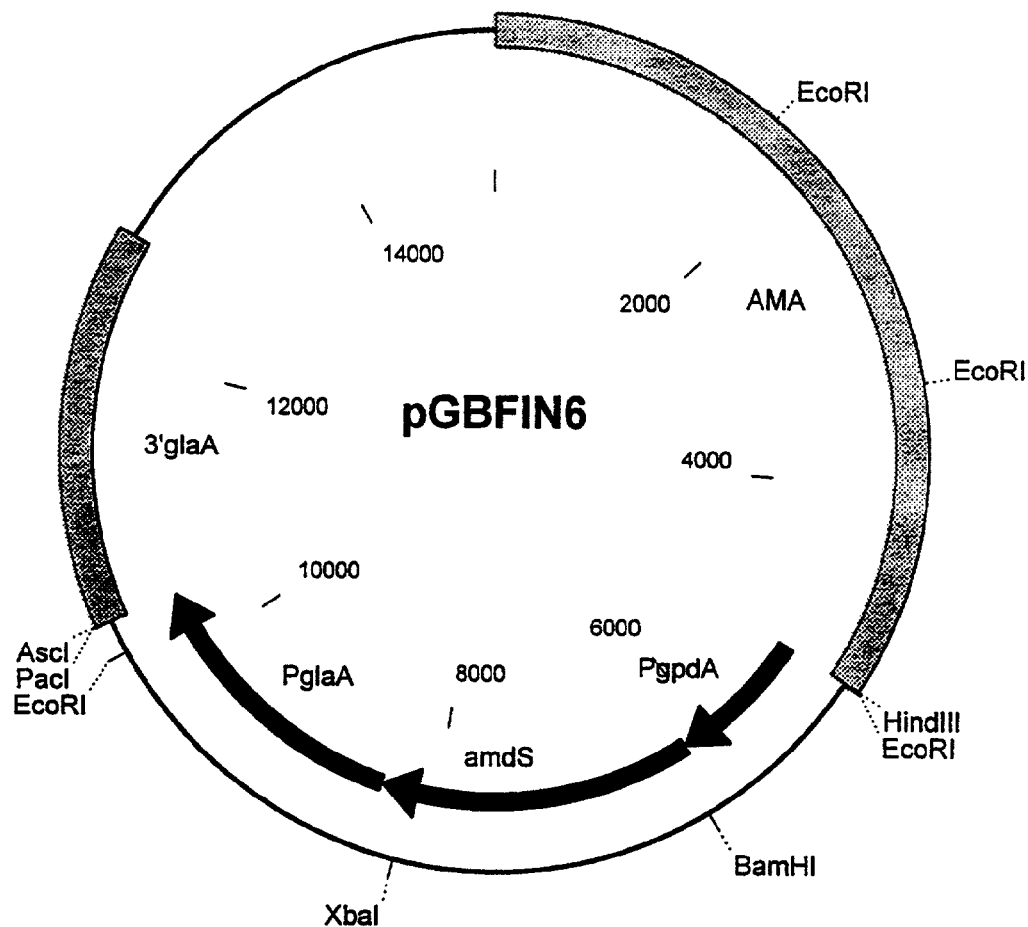
Figure 11: Physical map of pGBFin6 plasmid

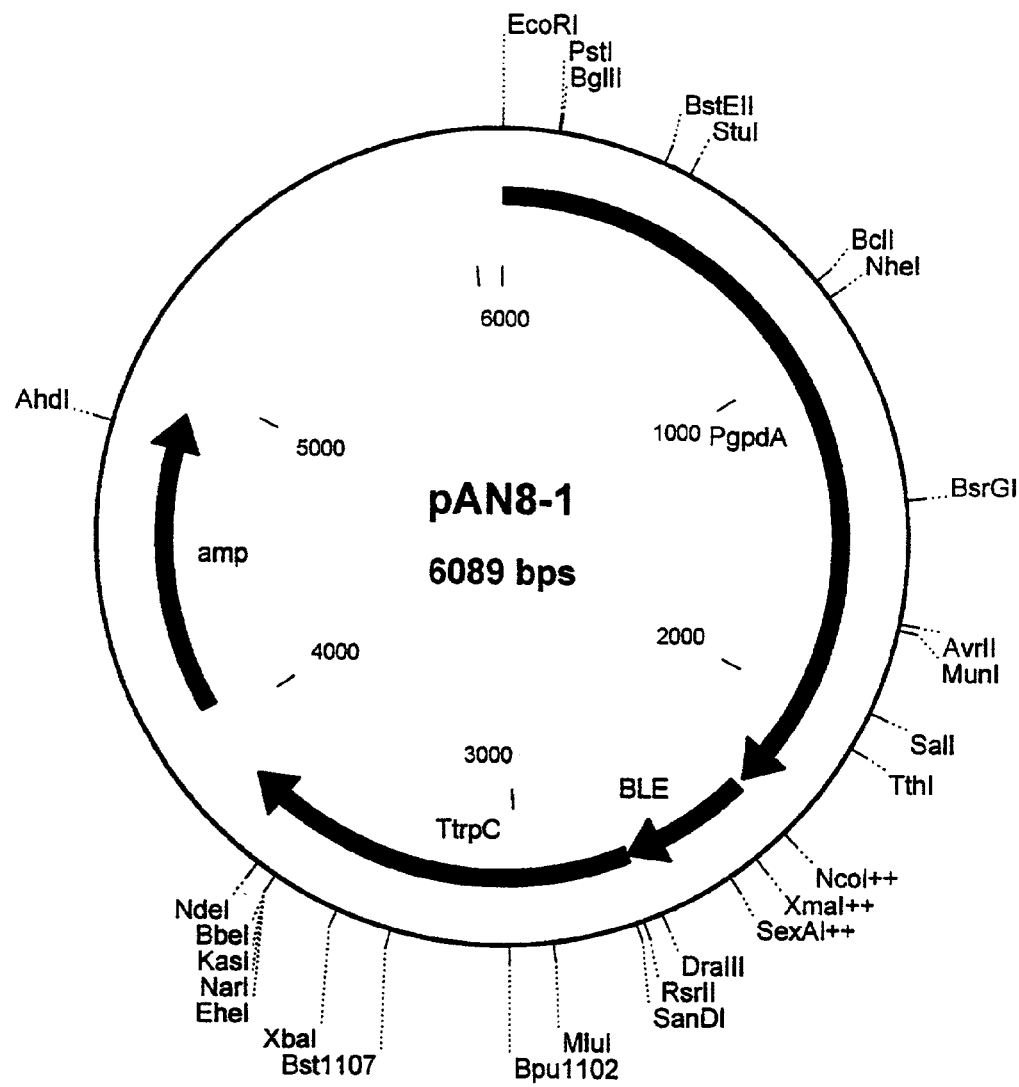
Figure 12: Physical map of pAN8-1

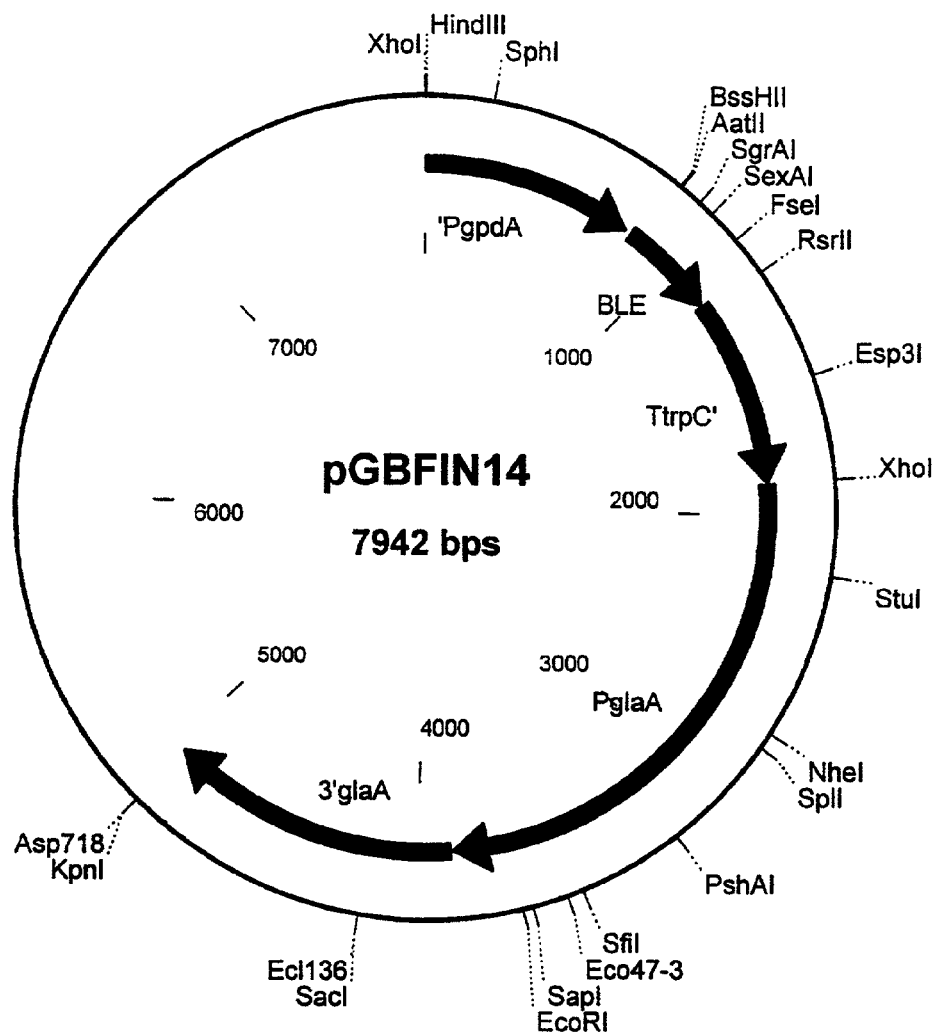
Figure 13: Physical map of pGBFin14 plasmid

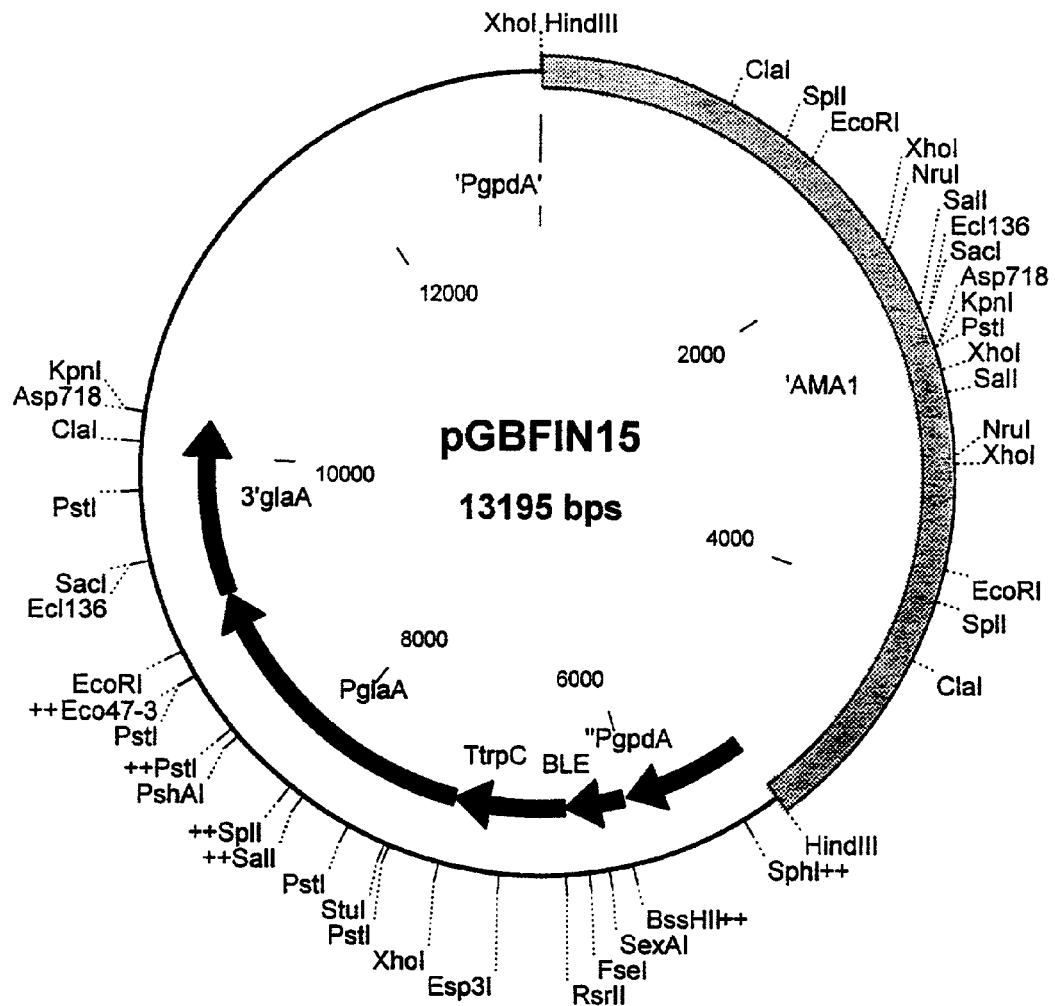
Figure 14: Physical map of pGBFin15 plasmid

SEQUENCE LISTING

<160> NUMBER OF SEQ ID NOS: 28

<210> SEQ ID NO 1
<211> LENGTH: 52
<212> TYPE: DNA
<213> ORGANISM: Artificial Sequence
<220> FEATURE:
<221> NAME/KEY: misc_feature
<223> OTHER INFORMATION: oligonucleotide 5288

<400> SEQUENCE: 1
tagtacgtag cgcccacaat caatccattt cgctatagtt aaaggatgcg ga         52

<210> SEQ ID NO 2
<211> LENGTH: 33
<212> TYPE: DNA
<213> ORGANISM: Artificial Sequence
<220> FEATURE:
<221> NAME/KEY: misc_feature
<223> OTHER INFORMATION: oligonucleotide 5289

<400> SEQUENCE: 2
gatcaggatc tccggatcaa tactccggcg tat                              33

<210> SEQ ID NO 3
<211> LENGTH: 33
<212> TYPE: DNA
<213> ORGANISM: Artificial Sequence
<220> FEATURE:
<221> NAME/KEY: misc_feature
<223> OTHER INFORMATION: oligonucleotide 5290

<400> SEQUENCE: 3
atacgccgga ctattcatcc ggagatcctg atc                              33

<210> SEQ ID NO 4
<211> LENGTH: 84
<212> TYPE: DNA
<213> ORGANISM: Artificial Sequence
<220> FEATURE:
<221> NAME/KEY: misc_feature
<223> OTHER INFORMATION: oligonucleotide 5291

<400> SEQUENCE: 4
cggaaagctt cactgacgta accaggaccc ggcggcttat ccatcatggg aaacaacacc  60
tacaaatccg ccacaatact ctcg                                        84

<210> SEQ ID NO 5
<211> LENGTH: 45
<212> TYPE: DNA
<213> ORGANISM: Artificial Sequence
<220> FEATURE:
<221> NAME/KEY: misc_feature
<223> OTHER INFORMATION: oligonucleotide 5292

<400> SEQUENCE: 5
gcaatcctcg aggtcccacc ggcaaacatc tgcccataga agaac                 45

<210> SEQ ID NO 6
<211> LENGTH: 88
<212> TYPE: DNA
<213> ORGANISM: Artificial Sequence
<220> FEATURE:
<221> NAME/KEY: misc_feature
<223> OTHER INFORMATION: oligonucleotide 5293

<400> SEQUENCE: 6
agtgaagctt tccgtggtac taagagagag gttactcacc gatggagccg tattcgccct  60
caagcaccgc gtgaccccac tattcgac                                    88

<210> SEQ ID NO 7
<211> LENGTH: 46
<212> TYPE: DNA
<213> ORGANISM: Artificial Sequence

```
<220> FEATURE:
<221> NAME/KEY: misc_feature
<223> OTHER INFORMATION: oligonucleotide 5358

<400> SEQUENCE: 7
aatttgcgcc cgcccgctcg agcggggaat tcccggtacg tacgca          46

<210> SEQ ID NO 8
<211> LENGTH: 46
<212> TYPE: DNA
<213> ORGANISM: Artificial Sequence
<220> FEATURE:
<221> NAME/KEY: misc_feature
<223> OTHER INFORMATION: oligonucleotide 5359

<400> SEQUENCE: 8
agcttgcgta cgtaccggga attccccgct cgagcgggcg gccgca          46

<210> SEQ ID NO 9
<211> LENGTH: 30
<212> TYPE: DNA
<213> ORGANISM: Artificial Sequence
<220> FEATURE:
<221> NAME/KEY: misc_feature
<223> OTHER INFORMATION: oligonucleotide 5361

<400> SEQUENCE: 9
ccaggacgcg gccgcttatc catcatggga                            30

<210> SEQ ID NO 10
<211> LENGTH: 29
<212> TYPE: DNA
<213> ORGANISM: Artificial Sequence
<220> FEATURE:
<221> NAME/KEY: misc_feature
<223> OTHER INFORMATION: oligonuceotide 5361

<400> SEQUENCE: 10
tagtacgtac aatcaatcca tttcgctat                             29

<210> SEQ ID NO 11
<211> LENGTH: 44
<212> TYPE: DNA
<213> ORGANISM: Artificial Sequence
<220> FEATURE:
<221> NAME/KEY: misc_feature
<223> OTHER INFORMATION: oligonucleotide 5367

<400> SEQUENCE: 11
cccaagcttg cggccgcgtc ctggttacgt cagtgatgtt tccg            44

<210> SEQ ID NO 12
<211> LENGTH: 25
<212> TYPE: DNA
<213> ORGANISM: Artificial Sequence
<220> FEATURE:
<221> NAME/KEY: misc_feature
<223> OTHER INFORMATION: oligonucleotide 5454

<400> SEQUENCE: 12
tccgcatgcc agaaagagtc accgg                                 25

<210> SEQ ID NO 13
<211> LENGTH: 25
<212> TYPE: DNA
<213> ORGANISM: Artificial Sequence
<220> FEATURE:
```

<221> NAME/KEY: misc_feature
<223> OTHER INFORMATION: oligonucleotide 5456

<400> SEQUENCE: 13
gcatccatcg gccaccgtca ttgga                                             25

<210> SEQ ID NO 14
<211> LENGTH: 39
<212> TYPE: DNA
<213> ORGANISM: Artificial Sequence
<220> FEATURE:
<221> NAME/KEY: misc_feature
<223> OTHER INFORMATION: oligonucleotide 6856

<400> SEQUENCE: 14
cggcagagta ggtgatagcg ttagaagaac cagtggtcc                              39

<210> SEQ ID NO 15
<211> LENGTH: 33
<212> TYPE: DNA
<213> ORGANISM: Artificial Sequence
<220> FEATURE:
<221> NAME/KEY: misc_feature
<223> OTHER INFORMATION: oligonucleotide 6963

<400> SEQUENCE: 15
acggaattca agctagatgc taagcgatat tgc                                    33

<210> SEQ ID NO 16
<211> LENGTH: 29
<212> TYPE: DNA
<213> ORGANISM: Artificial Sequence
<220> FEATURE:
<221> NAME/KEY: misc_feature
<223> OTHER INFORMATION: oligonucleotide 6964

<400> SEQUENCE: 16
ttaattaact cataggcatc atgggcgtc                                         29

<210> SEQ ID NO 17
<211> LENGTH: 32
<212> TYPE: DNA
<213> ORGANISM: Artificial Sequence
<220> FEATURE:
<221> NAME/KEY: misc_feature
<223> OTHER INFORMATION: oligonucleotide 6965

<400> SEQUENCE: 17
ggcgcgccga gtgtgattgt ttaaagggtg at                                     32

<210> SEQ ID NO 18
<211> LENGTH: 32
<212> TYPE: DNA
<213> ORGANISM: Artificial Sequence
<220> FEATURE:
<221> NAME/KEY: misc_feature
<223> OTHER INFORMATION: oligonucleotide 6967

<400> SEQUENCE: 18
atcatcggcg cgccttttttt tttttttttt tt                                    32

<210> SEQ ID NO 19
<211> LENGTH: 35
<212> TYPE: DNA
<213> ORGANISM: Artificial Sequence
<220> FEATURE:
<221> NAME/KEY: misc_feature

```
<223> OTHER INFORMATION: oligonucleotide 7423

<400> SEQUENCE: 19
ggaattctcg aggccgcaag ctcagcgtcc aattc                              35

<210> SEQ ID NO 20
<211> LENGTH: 35
<212> TYPE: DNA
<213> ORGANISM: Artificial Sequence
<220> FEATURE:
<221> NAME/KEY: misc_feature
<223> OTHER INFORMATION: oligonucleotide 7424

<400> SEQUENCE: 20
ggaattctcg agcacgcatg ggttgagtgg tatgg                              35

<210> SEQ ID NO 21
<211> LENGTH: 17
<212> TYPE: DNA
<213> ORGANISM: Artificial Sequence
<220> FEATURE:
<221> NAME/KEY: misc_feature
<223> OTHER INFORMATION: oligonucleotide 7676

<400> SEQUENCE: 21
taggccatat gggccat                                                  17

<210> SEQ ID NO 22
<211> LENGTH: 15
<212> TYPE: DNA
<213> ORGANISM: Artificial Sequence
<220> FEATURE:
<221> NAME/KEY: misc_feature
<223> OTHER INFORMATION: oligonucleotide 7677

<400> SEQUENCE: 22
ggcccatatg gccta                                                    15

<210> SEQ ID NO 23
<211> LENGTH: 23
<212> TYPE: DNA
<213> ORGANISM: Artificial Sequence
<220> FEATURE:
<221> NAME/KEY: misc_feature
<223> OTHER INFORMATION: xylB cDNA insert

<400> SEQUENCE: 23
cctcaagcca agtctctttc aac                                           23

<210> SEQ ID NO 24
<211> LENGTH: 12
<212> TYPE: DNA
<213> ORGANISM: Artificial Sequence
<220> FEATURE:
<221> NAME/KEY: misc_feature
<223> OTHER INFORMATION: xylB cDNA insert

<400> SEQUENCE: 24
gtctctttca ac                                                       12

<210> SEQ ID NO 25
<211> LENGTH: 25
<212> TYPE: DNA
<213> ORGANISM: Artificial Sequence
<220> FEATURE:
<221> NAME/KEY: misc_feature
<223> OTHER INFORMATION: xylB cDNA insert
```

```
<400> SEQUENCE: 25
ctcctcaagc caagtctctt tcaac                                              25

<210> SEQ ID NO 26
<211> LENGTH: 6
<212> TYPE: DNA
<213> ORGANISM: Artificial Sequence
<220> FEATURE:
<221> NAME/KEY: misc_feature
<223> OTHER INFORMATION: xylA cDNA insert

<400> SEQUENCE: 26 atcatc                                                                    6

<210> SEQ ID NO 27
<211> LENGTH: 33
<212> TYPE: DNA
<213> ORGANISM: Artificial Sequence
<220> FEATURE:
<221> NAME/KEY: misc_feature
<223> OTHER INFORMATION: xylA cDNA insert

<400> SEQUENCE: 27
aaaagccctt tactacttca tacatcaatc atc                                     33

<210> SEQ ID NO 28
<211> LENGTH: 22
<212> TYPE: DNA
<213> ORGANISM: Artificial Sequence
<220> FEATURE:
<221> NAME/KEY: misc_feature
<223> OTHER INFORMATION: xylB cDNA insert

<400> SEQUENCE: 28
ctcaagccaa gtctctttca ac                                                 22
```

US 7,220,542 B2

EXPRESSION CLONING IN FILAMENTOUS FUNGI

This is a continuation of application Ser. No. 09/555,998 now abandoned.

FIELD OF THE INVENTION

The present invention relates to methods for the identification of DNA sequences encoding proteins of interest by expression cloning using filamentous fungi as hosts.

BACKGROUND OF THE INVENTION

An increasing number of protein components with interesting properties is produced by means of recombinant DNA technology. Recombinant DNA production technology requires the availability of a DNA sequence coding for the protein component of interest. Conventional methods for cloning DNA sequences encoding proteins of interest have the drawback that each protein component has to be purified so as to allow determination of its (partial) amino acid sequence or, alternatively, to allow generation of specific antibodies. The (partial) amino acid sequences can then be used to design oligonucleotide probes for hybridisation screening. Alternatively, the specific antibodies are used for immunoscreening of expression libraries in *E. coli* such as e.g. lambda-gt11. Both methods require the purification and characterisation of the protein of interest which is a time consuming process. The cloning of novel protein components might therefore be considerably expedited by using a screening method involving selecting clones expressing a desired protein activity.

Such screening methods based on expression cloning have previously successfully been used for identification of prokaryotic gene products in e.g. *Bacillus* (cf. U.S. Pat. No. 4,469,791) and *E. coli* (e.g. WO 95/18219 and WO 95/34662). In some instances, also eukaryotic gene products have been identified using expression cloning in a bacterium like *E. coli* (e.g. WO 97/13853). However, in general prokaryotes are less suitable hosts for expression cloning of eukaryotic genes because many of these genes are not correctly expressed in bacteria. For example, eukaryotic genes often contain introns which are not spliced in bacteria. Although this splicing problem can be circumvented by using cDNAs of eukaryotic genes for expression cloning in bacteria, many eukaryotic gene products are not produced in active form in bacteria because the eukaryotic proteins are not correctly folded in bacteria or these proteins are rapidly degraded by bacterial proteases. Moreover, bacteria are generally incapable of efficiently secreting secreted eukaryotic proteins in active form and in contrast to eukaryotes, they do not have the ability to glycosylate proteins.

More recently a number of these problems have been overcome by using yeasts as hosts for expression cloning of eukaryotic genes. Strasser et al. (Eur. J. Biochem. (1989) 184: 699-706) have reported the identification of a fungal α-amylase by expression cloning of fungal genomic DNA in the yeast *Saccharomyces cerevisiae*. Similarly, WO 93/11249 reports the identification of a fungal cellulase by expression cloning of fungal cDNAs in *S. cerevisiae*. Yeasts are, however, known for their poor secretory capacity, particularly when compared to filamentous fungi. A number of secretory heterologous proteins are only poorly secreted from yeasts, if at all (see e.g. Kingsman et al., 1987, Trends Biotechnol. 5: 53-57). In addition yeasts are known to hyperglycosylate heterologous proteins (Innis, 1989, In: Yeast genetic Engineering, Barr, Brake & Valenzuela (eds), Butterworth, Boston, pp 233-246). Both poor secretion and hyperglycosylation are likely to interfere with expression cloning in yeast because it may significantly reduce the chance of detecting a given DNA sequence encoding a protein with properties of interest. This will apply in particular to DNA sequences encoding the many useful enzymes that are produced by eukaryotes such as filamentous fungi and which are often secreted and glycosylated. There is thus a need for an expression cloning system that would optimise the chance of detecting DNA sequences encoding secreted and possibly glycosylated proteins, and that is suitable for the identification of DNA sequences encoding proteins and enzymes produced by eukaryotes, of which in particular filamentous fungi. Alternatively, the expression cloning system should also be applicable to the identification of DNA sequences encoding eukaryotic or filamentous fungal proteins that are not secreted.

BRIEF DESCRIPTION OF THE FIGURES

FIG. 1: Construction of an intermediate expression vector, pGBTOP8. Details of this construction route are presented in the text.

FIG. 3: Physical map of pGBFin12.
FIG. 4: Physical map of pGBFin11.
FIG. 5: Physical map of pGBFin13.
FIG. 6: Physical map of pGBFin17.
FIG. 7: Physical map of pGBFin18.
FIG. 8: Physical map of pGBFin22.
FIG. 9: Physical map of pGBFin 19.
FIG. 10: Physical map of pGBFin23.
FIG. 11: Physical map of pGBFin6.
FIG. 12: Physical map of pAN8-1.
FIG. 13: Physical map of pGBFin14.
FIG. 14: Physical map of pGBFin15.

DESCRIPTION OF THE INVENTION

Figure 2A:
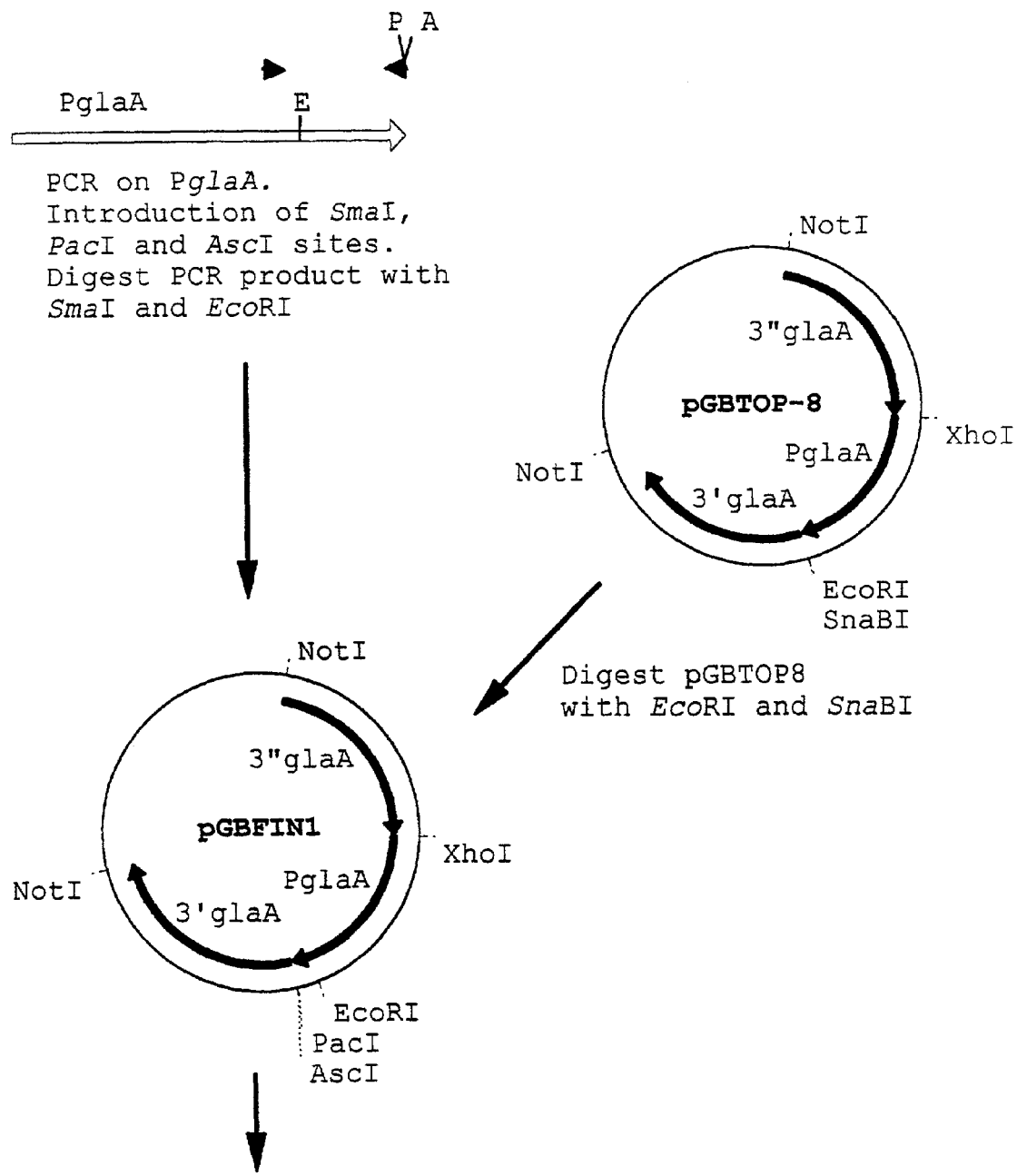
FIG. 2: Construction of expression vectors pGBFin2 and pGBFin5. Details of this construction route are presented in the text.

The present invention relates to a method for isolating DNA sequences coding for one or more proteins with properties of interest. The method preferably comprises the steps of: (a) preparing, in a suitable cloning vector, a DNA library from an organism suspected of being capable of producing one or more proteins with properties of interest; (b) transforming filamentous fungal host cells with the DNA library; (c) culturing the transformed host cells obtained in (b) under conditions conducive to the expression of the DNA sequences coding for proteins with properties of interest as present in the DNA library; and (d) screening for clones of the transformed host cells expressing a protein with properties of interest by analysis of the proteins produced in (c).

Any cloning vector capable of transforming a filamentous fungal host cell and capable of accepting DNA fragments from a DNA library is suitable for use in the method of the present invention. Cloning vectors for use in the present invention thus comprise integrative cloning vectors which integrate at random or at a predetermined target locus in the chromosomes of the filamentous fungal host cell, as well as autonomously maintained cloning vectors such as vectors based on the AMA1-sequence. In a preferred aspect of the invention, the integrative cloning vector comprises a DNA fragment which is homologous to a DNA sequence in a predetermined target locus in the genome of the filamentous fungal host cell for targeting the integration of the cloning vector to this predetermined locus. In order to promote targeted integration, the cloning vector is preferably linearized prior to transformation of the host cell. Linearization is preferably performed such that at least one but preferably either end of the cloning vector is flanked by sequences homologous to the target locus. The length of the homologous sequences flanking the target locus is preferably at least 0.5 kb, more preferably at least 1 kb, most preferably at least 2 kb. Integration of the cloning vector at a predetermined locus will promote uniformity of the expression levels of the individual clones in the library, thereby increasing the chance that each clone in the library is expressed at a detectable level. In a more preferred aspect of the invention, the DNA sequence in the cloning vector which is homologous to the target locus is derived from a gene which is capable of high level expression in the filamentous fungal host cell. A gene capable of high level expression, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/l.

In yet another preferred aspect of the invention the cloning vector comprises a promoter for expression of the DNA sequences coding for the protein with properties of interest in the library, whereby this promoter is preferably derived from a highly expressed filamentous fungal gene. The skilled person will appreciate the possibility that the homologous DNA sequence for targeting and the promoter sequence coincide in one DNA fragment.

A number of preferred highly expressed fungal genes are given by way of example: the amylase, glucoamylase, alcohol dehydrogenase, xylanase, glyceraldehyde-phosphate dehydrogenase or cellobiohydrolase genes from *Aspergilli* or *Trichoderma*. Most preferred highly expressed genes for these purposes are an *Aspergillus niger* glucoamylase gene, an *Aspergillus oryzae* TAKA-amylase gene, an *Aspergillus nidulans* gpdA gene or a *Trichoderma reesei* cellobiohydrolase gene. These highly expressed genes are suitable both as target loci for integration of cloning vectors and as source of highly expressed promoters from which the library fragments are expressed.

In another preferred embodiment the uniformity of the expression levels of the individual library clones is provided by the use of a cloning vector which is autonomously maintained in a filamentous fungus. An example of such an autonomously maintained cloning vector is disclosed in Example 8 which describes the construction and use of a cloning vector containing the AMA1-sequence. AMA1 is a 6.0-kb genomic DNA fragment isolated from *Aspergillus nidulans* which is capable of Autonomous Maintenance in *Aspergillus* (see e.g. Aleksenko and Clutterbuck (1997), Fungal Genet. Biol. 21: 373-397). AMA1-based cloning vectors for use in the method of the present invention provide the advantage of higher transformation frequencies as compared to integrative cloning vectors. AMA1-based cloning vectors also provide uniform expression of the individual library clones at reasonable levels which allow easy detection of the proteins with properties of interest in the library. However, the AMA1-based cloning vectors do require maintenance of selection pressure during growth of the transformants in order to avoid loss of the AMA1-based cloning vector due to its poor segregation.

The cloning vector may optionally further comprise a signal sequence operably linked to the promoter and upstream of a cloning site, so as to enable secretion of the proteins encoded by the DNA fragments in the library which are inserted into the cloning site. Secretion may facilitate detection of the proteins. In another embodiment of the invention the cloning vector contains a gene encoding a highly secreted protein, such as e.g. the *A. niger* glucoamylase gene. The highly secreted gene in the cloning vector contains a cloning site for insertion of the library fragments which is positioned such that the proteins encoded by the library fragments are produced as fusion-proteins with the highly secreted protein. This will improve their secretion in accordance with EP-A-0 429 628.

The selection marker gene in the cloning vector can be selected from a number of marker genes that are useful for transformation of filamentous fungi. By way of example these markers include but are not limited to amdS (acetamidase) genes, auxotrophic marker genes such as argB, trpC, or pyrG and antibiotic resistance genes providing resistance against e.g. phleomycin, hygromycin B or G418. In a preferred aspect of the invention the cloning vector comprises a selection marker gene which is expressed by the fungal host cell at sufficient levels during selection of transformants so as to avoid a bias for transformants with multiple copies of the cloning vector integrated into the host cell's genome. A preferred selection marker gene for this purpose is the *A. nidulans* amdS coding sequence fused to the *A. nidulans* gpdA promoter.

The host cell of the present invention is a filamentous fungus which is capable of being transformed with a cloning vector. For most filamentous fungi tested thus far it was found that they could be transformed using transformation protocols developed for *Aspergillus* (derived from inter alia Tilburn et al. 1983, Gene 26:205-221). The skilled person will recognise that successful transformation of the filamentous fungal host species is not limited to the use of vectors, selection marker systems, promoters and transformation protocols specifically exemplified herein.

A filamentous fungus is herein defined as an eukaryotic micro-organism of the subdivision Eumycotina in filamentous form, i.e. the vegetative growth of which occurs by hyphal elongation. Preferred filamentous fungal host cells are selected from the group consisting of the genera *Aspergillus, Trichoderma, Fusarium, Penicillium,* and *Acremonium*. In another preferred embodiment, e.g. when the protein of interest is a thermophilic protein, preferred filamentous fungal host cells are selected from the group of thermophilic fungi consisting of the genera *Talaromyces, Thielavia, Myceliophtora, Thermoascus, Sporotrichum, Chaetomium, Ctenomyces,* and *Scytalidium*.

In a more preferred embodiment of the invention the filamentous fungal host cell is selected from the group consisting of *A. nidulans, A. oryzae, A. sojae, Aspergilli* of the *A. niger* Group and *Trichoderma reesei*. The *A. niger* Group is herein defined according to Raper and Fennell (1965, In: The Genus *Aspergillus*, The Williams & Wilkins Company, Baltimore, pp 293-344) and comprises all (black) *Aspergilli* therein included by these authors.

In yet a further preferred aspect of the invention the filamentous fungal host cell, at least when used in the method of the invention in combination with an integrative cloning vector comprising a DNA fragment which is homologous to a DNA sequence in a predetermined target locus, comprises multiple copies of the predetermined target locus. More preferably the host cell comprises multiple copies of a target locus comprising a highly expressed gene, such as the highly expressed fungal genes exemplified above. The advantage of host cells with multiple copies of the target locus is that the use of these host cells increases the frequency of integrative targeted transformation, thus increasing the chance of obtaining efficiently expressing transformants for each individual clone in the library.

The organism suspected of producing one or more proteins with properties of interest usually is an eukaryote, preferably a fungus, of which most preferably a filamentous fungus. These organisms are known to produce a large variety of proteins that are useful for industrial applications.

In the method according to the invention, the library of DNA fragments from an organism suspected of producing one or more proteins with properties of interest can be a genomic library or a cDNA library. However, preferably a cDNA library is used so as to avoid problems with recognition of promoters or splice signals in the host organism. The cDNA library is preferably prepared from mRNA isolated from the source organism when grown under conditions conducive to the expression of the proteins with properties of interest.

The method according to the invention can be applied to the isolation of DNA sequences coding for any protein with properties of interest if there is an assay available for detection of the protein when expressed by the fungal host cell. Preferably the protein with properties of interest is an enzyme. Examples of enzymes which may be identified by the method of the invention are carbohydrases, e.g. cellulases such as endoglucanases, β-glucanases, cellobiohydrolases or β-glucosidases, hemicellulases or pectinolytic enzymes such as xylanases, xylosidases, mannanases, galactanases, galactosidases, rhamnogalacturonases, arabanases, galacturonases, lyases, or amylolytic enzymes; phosphatases such as phytases, esterases such as lipases, proteolytic enzymes, oxidoreductases such as oxidases, transferases, or isomerases.

After transformation of the filamentous fungal host cells with the DNA library the transformed clones are screened for expression of the protein with properties of interest. Depending on the assay required for detection of the protein with properties of interest the transformed clones are propagated and stored as colonies on solid media such as agar plates or in liquid media, whereby the individual library clones are grown, stored and/or assayed in the wells of the microtiter plates.

A large variety of systems for detection of the proteins with properties of interest are known to the skilled person. Because the library clones can be grown on solid as well as in liquid media, detection systems include any possible assay for detection of proteins or enzymatic activity. By way of example these assay systems include but are not limited to assays based on clearing zones around colonies on solid media, as well as colorimetric, photometric, turbidimetric, viscosimetric, immunological, biological, chromatographic, and other available assays.

The skilled person will understand that the usual adaptations to cloning methods known in the art can equally be applied to the method of the present invention. The adaptations include but are not limited to e.g. screening of pools of library clones, screening the same library for a number of different proteins with properties of interest, as well as rescreening, reisolation and recloning of positive clones to ensure more accurate results.

A variety of methods are available to the skilled person for isolation of the DNA sequence encoding the protein with properties of interest from the transformed host cell identified in the screening method, and for subsequent characterization of the isolated DNA sequence.

The DNA sequences isolated by the screening method of the invention as described above are used to produce, or to improve the production of, a protein with properties of interest encoded by the DNA sequence. Advantageously, the transformed filamentous fungal host cell as isolated in the above described screening method is used directly in a process for the production of the protein with properties of interest by culturing the transformed host cell under conditions conducive to the expression of the protein of interest and, optionally, recovering the protein. However, often the initial transformed host cell isolated in the screening method of the invention will have an expression level which is satisfactory for screening purposes but which can be significantly improved for economic production purposes. To this end the DNA sequence is inserted into an expression vector which is subsequently used to transform a suitable host cell. In the expression vector the DNA sequence is operably linked to appropriate expression signals, such as a promoter, optionally a signal sequence and a terminator, which are capable of directing the expression of the protein in the host organism. A suitable host cell for the production of the protein is preferably a yeast or a filamentous fungus. Preferred yeast host cells are selected from the group consisting the genera *Saccharomyces, Kluyveromyces, Yarrowia, Pichia*, and *Hansenula*. Preferred filamentous fungal host cells are selected from the same genera listed above as preferred host cells for the screening method. Most preferred filamentous fungal host cells are selected from the group consisting of *Aspergilli* of the *A. niger* Group, *A. oryzae*, and *Trichoderma reesei*. The suitable host cell is transformed with the expression vector by any of the various protocols available to the skilled person. The transformed host cell is subsequently used in a process for producing the protein of interest by culturing the transformed host cell under conditions conducive to the expression of the DNA sequence encoding the protein, and recovering the protein.

The present invention is further illustrated by the following examples.

EXAMPLES

| Nomenclature | |
|---|---|
| phyA | *A. ficuum* phyA gene, encoding phytase. |
| xylA | *A. tubigensis* xylA gene, encoding xylanase |
| amdS | *A. nidulans* amdS gene, encoding acetamidase (Corrick et al., 1987 Gene 53: 63–71) |
| glaA | *A. niger* glaA gene encoding glucoamylase |
| gpdA | *A. nidulans* gpdA gene, encoding glyceraldehyde 3-phosphate dehydrogenase (Punt et al., 1988 Gene 69: 49–57) |
| $P_{gpdA}$ | gpdA promoter |
| $P_{glaA}$ | glaA promoter |
| $T_{amdS}$ | amdS terminator |
| $T_{glaA}$ | glaA terminator |
| GLA | *A. niger* glucoamylase protein |

| Abbreviations | |
|---|---|
| kb | kilo base |
| bp | base pair |
| oligo | oligonucleotide |

-continued

| Abbreviations | |
|---|---|
| PCR | Polymerase Chain Reaction |
| PDA | Potato Dextrose Ajar |

Oligonucleotides Used

The oligonucleotides used in examples 1-3 are listed in the SEQUENCE LISTING.

Materials and Methods

General Procedures

Standard molecular cloning techniques such as DNA isolation, gel electrophoresis, enzymatic restriction modifications of nucleic acids, Southern analyses, E. coli transformation, etc., were performed as described by Sambrook et al. (1989) "Molecular Cloning: a laboratory manual", Cold Spring Harbor Laboratories, Cold Spring Harbor, N.Y. and Innis et al. (1990) "PCR protocols, a guide to methods and applications" Academic Press, San Diego. Synthetic oligo deoxynucleotides were obtained from ISOGEN Bioscience (Maarssen, The Netherlands). DNA sequence analyses were performed on an Applied Biosystems 373A DNA sequencer, according to supplier's instructions.

DNA Labeling and Hybridizations

DNA labeling and hybridizations were according to the ECL™ direct nucleic acid labeling and detection systems (Amersham LIFE SCIENCE, Little Chalfont, England or according to the standard radioactive labeling techniques as described in Sambrooke et al 1989).

Transformation of *Aspergillus niger*.

Transformation of *A. niger* was performed according to the method described by Tilburn, J. et al. (1983) Gene 26, 205-221 and Kelly, J. & Hynes, M. (1985) EMBO J., 4, 475-479 with the following modifications: Spores were grown for 16 hours at 30° C. in a rotary shaker at 300 rpm in *Aspergillus* minimal medium. *Aspergillus* minimal medium contains per liter: 6 g $NaNO_3$, 0.52 g KCl, 1.52 g $KH_2PO_4$, 1.12 ml 4 M KOH, 0.52 g $MgSO_4.7H_2O$, 10 g glucose, 1 g casaminoacids, 22 mg $ZnSO_4.7H_2O$, 11 mg $H_3BO_3$, 5 mg $FeSO_4.7H_2O$, 1.7 mg $COCl_2.6H_2O$, 1.6 mg $CuSO_4.5H_2O$, 5 mg $MnCl_2.2H_2O$, 1.5 mg $Na_2MoO_4.2H_2O$, 50 mg EDTA, 2 mg riboflavin, 2 mg thiamine-HCl, 2 mg nicotinamide, 1 mg pyridoxine-HCL, 0.2 mg panthotenic acid, 4 g biotin, 10 ml Penicillin (5000 IU/ml) Streptomycin (5000 UG/ml) solution (Gibco).

Novozym 234™ (Novo Industries) instead of helicase was used for the preparation of protoplasts;

after protoplast formation (60-90 minutes), KC buffer (0.8 M KCl, 9.5 mM citric acid, pH 6.2) was added to a final volume of 45 ml, the protoplast suspension was centrifuged for 10 minutes at 3000 rpm at 4 C in a swinging-bucket rotor. The protoplasts were resuspended in 20 ml KC buffer and subsequently 25 ml of STC buffer (1.2 M sorbitol, 10 mM Tris-HCl pH 7.5, 50 mM $CaCl_2$) was added. The protoplast suspension was centrifuged for 10 minutes at 3000 rpm at 4 C in a swinging-bucket rotor, washed in STC-buffer and resuspended in STC-buffer at a concentration of $10^8$ protoplasts/ml;

to 200 l of the protoplast suspension, the DNA fragment, dissolved in 10 l TE buffer (10 mM Tris-HCl pH 7.5, 0.1 mM EDTA) and 100 l of a PEG solution (20% PEG 4000 (Merck), 0.8 M sorbitol, 10 mM Tris-HCl pH 7.5, 50 mM $CaCl_2$) was added;

after incubation of the DNA-protoplast suspension for 10 minutes at room temperature, 1.5 ml PEG solution (60% PEG 4000 (Merck), 10 mM Tris-HCl pH 7.5, 50 mM $CaCl_2$) was added slowly, with repeated mixing of the tubes. After incubation for 20 minutes at room temperature, suspensions were diluted with 5 ml 1.2 M sorbitol, mixed by inversion and centrifuged for 10 minutes at 4000 rpm at room temperature. The protoplasts were resuspended gently in 1 ml 1.2 M sorbitol and plated onto selective regeneration medium consisting of either *Aspergillus* minimal medium without riboflavin, thiamine.HCL, nicotinamide, pyridoxine, panthotenic acid, biotin, casaminoacids and glucose, in the case of acetamide selection supplemented with 10 mM acetamide as the sole nitrogen source and 1 M sucrose as osmoticum and C-source, or, on PDA supplemented with 1-30 µg/ml phleomycin and 1M sucrose as osmosticum in the case of phleomycin selection. Regeneration plates were solidified using 2% Oxoid No. 1 agar. After incubation for 6-10 days at 30° C., conidiospores of transformants were transferred to plates consisting of *Aspergillus* selective medium (minimal medium containing acetamide as sole nitogen source in the case of acetamide selection or PDA supplemented with 1-30 µg/ml phleomycin in the case of phleomycin selection) with 2% glucose instead of sucrose and 1.5% agarose instead of agar and incubated for 5-10 days at 30° C. Single transformants were isolated and this selective purification step was repeated once upon which purified transformants were stored.

Direct PCR on Fungal Mycelium

Transformants were incubated on PDA-containing plates for two days at 30° C. Approximately one third of a colony was incubated for 2 h at 37° C. in 50 l KC buffer (60 g/l KCl, 2 g/l citric acid, pH 6.2), supplemented with 5 mg/ml Novozym™ 234. Subsequently 100 l (10 mM Tris, 50 mM EDTA, 150 mM NaCl, 1% SDS, pH8) and 400 l QIAquick™ PB buffer (Qiagen Inc., Chatsworth, USA) was added. Extracts were gently resuspended and loaded onto a QIAquick™ spin column. Columns were centrifuged for 1 min at 13000 rpm in a microfuge and washed once with 500 I QIAquick™ PE buffer. Traces of ethanol were removed by a final quick spin. Chromosomal DNA (PCR template) was eluted from the column by addition of 50 l $H_2O$ and subsequent centrifugation for 1 min at 13000 rpm. PCR reactions contained 10 l eLONGase™ B buffer (Life Technologies, Breda, The Netherlands), 14 l dNTP s (1.25 mM each), 1 l eLONGase™ Enzyme Mix, 1 l template, and 10-30 pmol of each oligo, in a final volume of 50 l. The optimal amount of oligo s was determined experimentally for each purchased batch. On average, 10 to 30 pmol was used. Reactions were performed with the following cycle conditions: 1×(2 min)94° C., 10× (15 sec 94° C., 30 sec 55° C., 4 min 68° C.), 20× (15 sec 94° C., 30 sec, 55° C. 4 min. start with incline of 20 sec per cycle, 68° C.), 1× (10 min 68° C.). Samples were loaded on agarose gels for analyses of PCR products.

*Aspergillus niger* Shake Flask Fermentations.

Of recombinant and control *A. niger* strains a large batch of spores were generated by plating spores or mycelia onto selective medium plates or PDA-plates (Potato Dextrose Agar, Oxoid), prepared according to the supplier's instructions. After growth for 3-7 days at 30° C. spores were collected after adding 0.01% Triton X-100 to the plates. After washing with sterile demineralized water about $10^7$ spores of selected transformants and control strains were inoculated into shake flasks, containing 20 ml of liquid preculture medium containing per liter: 30 g maltose.$H_2O$, 5 g yeast extract, 10 g hydrolyzed casein, 1 g $KH_2PO_4$, 0.5 g $MgSO_4.7H_2O$, 0.03 g $ZnCl_2$, 0.02 g $CaCl_2$, 0.01 g $MnSO_4.4H_2O$, 0.3 g $FeSO_4.7H_2O$, 3 g Tween 80, 10 ml penicillin (5000 IU/ml)/Streptomycin (5000 UG/ml), pH 5.5 and 1-30 µg/ml phleomycin in the case of phleomycin selection. These cultures were grown at 34° C. for 20-24 hours. 10 ml of this culture was inoculated into 100 ml of A. niger fermentation medium containing per liter: 70 g glucose, 25 g hydrolyzed casein, 12.5 g yeast extract, 1 g $KH_2PO_4$, 2 g $K_2SO_4$, 0.5 g $MgSO_4.7H_2O$, 0.03 g $ZnCl_2$, 0.02 g $CaCl_2$, 0.01 g $MnSO_4.4H_2O$, 0.3 g $FeSO_4.7H_2O$, 10 ml penicillin (5000 IU/ml)/Streptomycin (5000 UG/ml), adjusted to pH 5.6 with 4 N $H_2SO_4$, and 1-30 µg/ml phleomycin in the case of phleomycin selection. These cultures were grown at 34° C. for 6 days. Samples taken from the fermentation broth were centrifuged (10', 5.000 rpm in a swinging bucket centrifuge) and supernatants collected. Xylanase or phytase activity assays (see below) were performed on these supernatant.

Phytase Activity Assay.

20 µl supernatant (diluted when necessary) of shake flask Aspergillus niger fermentations (as reference 20 l demineralized water) is added to 30 l substrate mix, containing 0.25 M sodium acetate buffer pH 5.5, 1 mM phytic acid (sodium salt, Sigma P-3168), in a 96 wells microtiter dish, and incubated for 25 minutes at room temperature. The reaction is stopped by the addition of 150 l stop mix (14.6 g $FeSO_4.7H_2O$ in 300 ml of 0.67% $(NH_4)_6Mo_7O_{240}.4H_2O$, 2% $H_2SO_4$, 3.3% Trichloroacetic acid). After incubation at room temperature for 5 minutes the absorbance of the blue color is measured spectrophotometrically at 690 nm in an Anthosreader (Proton and Wilton). The measurements are indicative of phytase activity in the range of 0-175 U/ml. Phytase activity was measured as described in EPO 0 420 358 A.

Xylanase Activity Assays

Supernatant (pre-diluted when necessary) is diluted 5 times in 0.25 M sodium acetate buffer, pH 4.5. 20 µl of diluted supernatant is transferred to microtiter dishes and 50 µl substrate (4% w/v Remazol Brilliant Blue RBB-Xylan dissolved at 70° C. in demineralized water) is added and mixed thoroughly by pipetting up and down. The reaction is incubated for 30 minutes at room temperature. The reaction is stopped by addition of 200 l 96% ethanol and incubated for 10 minutes at room temperature. After the reaction has been terminated the microtiter plates are centrifuged for 10 minutes at 2500 rpm in a Beckman GPK centrifuge at room temperature. 100 l of the supernatant is transferred to a new microtiter dish and absorbance of the blue colour is measured spectrophotometrically at 620 nm in an Anthosreader (Proton and Wilton). Specific activity is calculated from a calibration curve using a xylanase standard dissolved in 0.25 M sodium acetate buffer pH 4.5. The measurements are indicative of xylanase activity in the range of 0-150 EXU/ml. Units of xylanase activity are defined as in EP 0 463 706.

RNA Isolation

A. tubigensis strain DS116813 (CBS323.90) was cultured in Aspergillus minimal medium (per liter 6 g $NaNO_3$, 0.52 g KCl, 1.52 g $KH_2PO_4$, 1.12 ml 4 M KOH, 0.52 g $MgSO_4.7H_2O$, 22 mg $ZnSO_4.7H_2O$, 11 mg $H_3BO_3$, 5 mg $FeSO_4.7H_2O$, 1.7 mg $CoCl_2.6H_2O$, 1.6 mg $CuSO_4.5H_2O$, 5 mg $MnCl_2.2H_2O$, 1.5 mg $Na_2MoO_4.2H_2O$, 50 mg EDTA, 10 g glucose) supplemented with 0.1% yeast extract and 3% oat spelt xylan (Serva). 100 ml medium was inoculated with 2.108 spores and cultured in a rotary shaking incubator at 30° C. and 300 rpm for 48 hours. Mycelium was harvested by filtration using Miracloth filtration wrap, washed extensively with demineralized water and squeezed between paper towels to remove excessive water. Mycelium was frozen immediately in liquid nitrogen and grinded to a fine powder using mortar and pestle. The resulting powder was transferred to a sterile 50 ml tube and weighed upon which for every 1-1.2 g of ground mycelium 10 ml TRIzol reagent (Gibco/BRL) was added (max. 25 ml per tube). The mycelial powder was immediately solubilized by vigorous mixing (vortexing, 1 min.), followed by 5 min room temperature incubation with occasional mixing. 0.2 (original TRIzol) volume of chloroform (thus 2 ml for every 10 ml TRIzol used originally) was added, vortexed and left at room temperature for 10 min. Subsequently, the mixture was centrifuged at 4° C., 6000 g for 30 minutes. The top aqueous phase was transferred to a fresh tube and total RNA was precipitated by addition of 0.5 (original TRIzol) volume of isopropyl alcohol (thus 5 ml of isopropyl alcohol for every 10 ml TRIzol used originally). After 10 minutes precipitation at room temperature, the RNA was recovered by centrifugation for 30 minutes at 6000 g. Upon removal of supernatant the RNA pellet was rinsed with one volume of 70% ethanol. After removal of the ethanol, the RNA pellet was air dried. The dried RNA pellet was dissolved in 3 ml GTS (100 mM Tris-Cl, pH 7.5, 4 M guanidium thiocyanate, 0.5% sodium lauryl sarcosinate) buffer. 10 µl of RNA solution was used to determine quality and concentration of nucleic acids.

RNA Purification Via Centrifugation in CsCl Solution

The isolated RNA was further purified by a modification of the method described by Sambrooke et al. (Molecular cloning, second edition, Cold Spring Harbor Laboratory, 1989).

A CsCl/EDTA solution was prepared by dissolving 96 g CsCl in 70 ml 10 mM EDTA, pH 7.5. DEPC was added to a final concentration of 0.1%. The solution was left for 30 min at room temperature and subsequently autoclaved for 20 min at 15 pounds per square inch (psi) on liquid cycle. Upon cooling down of the solution the volume was adjusted to 100 ml with DEPC-treated water. 1.5 ml of this CsCl/EDTA solution was added to each Polyallomer (2"x0.5", 5 ml capacity) ultracentrifuge tubes. 3 ml of RNA samples (in GTS) were layered on the 1.5 ml CsCl/EDTA cushion. Ultracentrifuge tubes were filled to within 5 mm from the top with GTS. Filled ultracentrifuge tubes were balanced accurately with GTS and placed in matching ultracentrifuge buckets. Ultracentrifuge tubes were centrifuged at 35.000 rpm for 18 h at 20° C. with slow acceleration and turned off brake for deceleration. After centrifugation the top layer above the CsCl cushion, and part of the cushion were removed with clean pasteure pipettes, respectively (0.5 cm CsCl cushion is left in the tube). The bottom of the tube was cut of with a heated razor blade upon which remaining fluid was removed. The bottom of the tube was filled with 70% ethanol at room temperature. The bottom of the tube was inverted and the RNA pellet was air dried. The RNA pellet was dissolved in 1 ml of TE (elution buffer of the PHARMACIA mRNA purification kit; see mRNA isolation). Again 10 µl was taken to check quality and quantity.

mRNA Isolation

For isolation of mRNA a modified protocoll (using gravity flow instead of centrifugation) of the PHARMACIA purification kit (Cat#27-9258-02) was used.

The PHARMACIA column was completely resuspended by repeated inversion upon which the column was packed via gravity flow. The column was placed at a temperature of 50° C. and washed with 1 ml of High Salt Buffer. The RNA solution (in TE) was heated up at 65° C. for 5 min. upon which 200 µl of sample buffer was added and the RNA solution was loaded on the column. The flowthru was collected and reloaded on the column. The column was washed 3 times with 0.5 ml of High Salt Buffer and subsequently several times with 0.5 ml of Low Salt Buffer until no UV-absorbing material was being eluted from the column. The poly(A)$^+$RNA was eluted with prewarmed (65° C.) Elution Buffer from which 4-5 0.25 ml fractions were collected. Concentrations of the various fractions were determined spectrophotometrically and fractions with an O.D. 260/280 ratio of at least 1.5 were pooled. 0.1 volume of Sample Buffer and 2 volumes of absolute ethanol were added and the solution was incubated overnight at −20° C.

Northern Analysis

RNA was separated by electrophoresis on a 1% agarose gel containing 6% formaldehyde and using 1×MOPS (20 mM MOPS/pH7.0, 1 mM EDTA) as electrophoresis buffer. Samples (approximately 10 g total RNA or 1 g mRNA) were dissolved in a total volume of 20 1 loading buffer (final concentrations: 20 mM MOPS/pH 7.0, 1 mM EDTA, 6% formaldehyde, 50% formamide, 0.05 g ethidiumbromide) and denatured by heating at 68° C. for 10 minutes. After electrophoresis for 3-4 hours at 100 Volt, RNA was visualised using an UV illuminator. For Northern analysis the gel was washed for 20 minutes in demineralized water and transferred to Hybond-N$^+$ (Amersham) nylon membrane by capillary blotting. RNA was fixed to the membrane by baking at 80° C. for 2 hours. Specific transcripts were detected using the ECL™ system or standard radioactive labelling techniques as described in Sambrooke et al. 1989.

Analysis of cDNA by Electrophoresis on an Alkaline Agarose Gel

This control analysis step revealed the size of the cDNA synthesized and was used as a check for the potential presence of hairpin structure. Since the specific activity of the second-strand synthesis was much lower than that of the first-strand synthesis, the volume of the second-strand synthesis used was 10 times that of the first-strand synthesis.

A thin 1% agarose gel was prepared by melting 0.6 g agarose in 54 ml water, cooling to 55° C., adding 6 ml of 10× alkaline buffer (0.3 M NaOH, 20 mM EDTA), mixing and casting. Samples were mixed (1:1) with 2× alkaline gel loading buffer (30 mM NaOH, 20% glycerol, $\frac{1}{10}$ volume saturated bromophenol blue). Samples were run (alongside $^{32}$P-labelled molecular weight markers) in 1× alkaline buffer. The gel was fixed for 30 min in 7% acetic acid and blotted on Whatman 3 MM paper and dried. The dried gel was exposed to X-ray film which was developed in an automatic film processor.

cDNA Synthesis

For cDNA synthesis both the Superscript™ choice system (Gibco-BRL) and the STRATAGENE cDNA Synthesis KIT have been used.

When cDNA was synthesised with the Superscript™ choice system 5 µg mRNA was used according to the instructions of the manufacturer except that oligonucleotide 6967 was used for first strand synthesis and that oligonucleotides 7676 (5'-phosphorylated) and 7677 (non-phosphorylated) were used as adapter. Annealing of oligonucleotides 7676 and 7677 was achieved by mixing equimolar amounts of both oligonucleotides in 10 mM Tris-HCl/pH 7.5, 1 mM EDTA, 1 mM MgCl$_2$. The mixture was incubated in a 80° C. waterbath for 10 minutes after which the water was allowed to cool down slowly to room temperature.

For cDNA synthesis with the Strategene cDNA Synthesis Kit the protocoll has optimized for cloning in the pGBFIN vectors described. Major changes were: 1) The amount of cDNA synthesized was quantified by TCA precipitation. 2) Phosphorylation of the ends of the cDNAs was omitted and cDNAs were ligated to vector DNA with phosphorylated ends. 3) The cDNA is extracted with phenol/chloroform after digestion with XhoI rather than after size fractionation. 4) The use of both MMLV-RT (STRATAGENE) and THERMOSCRIPT (Gibco/BRL) in the first strand synthesis consistently result in cDNAs with longer lengths than the use of either enzyme alone. 5.) control reactions traced with [alpha$^{32}$P]dATP (800 Ci/mmol in order to prevent interference with synthesis) were performed alongside for quality control;

first-strand components and poly(A)$^+$RNA were combined and mixed according to protocol and left for 10 min. at room temperature to allow primer-template annealing.

1.5 ul of MMLV-RT (50 U/ul) and 1 ul of THERMOSCRIPT (15 U/ul, GibcoBRL) was added to the first-strand reaction to obtain a 50 ul final reaction volume. Upon mixing 5 ul of the reaction mixture was taken and added to 0.5 ul of [alpha$^{32}$P]dATP (800 Ci/mmol) to obtain a radioactive first-strand control reaction. The first-strand synthesis reactions were incubated at 37° C. for 0.5 hour followed by 55° C. for 0.5 hour.

The non radioactive first-strand synthesis reaction was placed on ice and 20 ul of 10× second-strand buffer, 6 ul of second-strand dNTP mixture, 114 ul of sterile distilled water, 2 ul of [alpha$^{32}$P]dATP (800 Ci/mmol), 2 ul of RNase H (1.5 U/ul) and 11 ul of DNA polymerase 1 (9.0 U/ul) were added. Upon mixing the reaction mixture was incubated at 16° C. for 2.5 hours. After incubation, 10 ul was removed and frozen.

Estimation Amount cDNA Synthesized by TCA Precipitation 1 ul of from the first-strand radioactive (control) reaction was mixed with 20 ul of water. Similarly, 2 ul of the second-strand synthesis reaction was mixed with 20 ul of water. 5 ul of the thus obtained solutions were spotted (4× for each control solution) on Whatmann glass fibre filters (GF/C or GF/A, 23 mm diameter) and air dried. The filters were transferred to 200 ml of ice-cold 5% of trichloroacetic acid (TCA) and 20 mM sodium pyrophosphate. The ice-cold TCA/sodium pyrophosphate solution was changed 3-4 times every 2 min. The filters were rinsed with 70% ethanol at room temperature for 2 min. Each filter was inserted into a scintillation vial, 10 ml of scintillant was added and the radioactive material was counted upon which specific activity of the cDNA was calculated.

Blunting the cDNA Termini and Ligation of Adapters

To the second-strand synthesis reaction 23 ul of blunting dNTP mix and 2 ul of Pfu DNA polymerase (2.5 U/ul) was added upon which the reaction mixture was incubated at 72° C. for 30 min. The reaction mixture was phenol/chloroform-extracted [200 ul solution 1:1 (v/v), pH 7-8], chloroform extracted [200 ul] and the cDNA was precipitated by adding 20 ul of 3 M sodium acetate and 400 ul of absolute ethanol followed by overnight incubation at −20° C. The cDNA was collected via centrifugation, washed with 70% ethanol and the obtained cDNA pellet was air dried and resuspended in 8 ul of adapter solution. 1 ul of 10× ligase buffer, 1 ul of rATP and 1 ul of T4 DNA ligase were added and the ligation mixture was incubated either at 8° C. overnight or at 4° C. for 2 days. Next, the ligase was inactivated by incubation at 70° C. for 30 min.

Restriction Enzyme Digestion of cDNAs and Size Fractionation 10 ul of sterile water (to compensate for the volume in the omitted phosphorylation step), 28 ul of restriction enzyme buffer and 3 ul of restriction enzyme (40 U/ul) were added to the cDNA. The reaction was incubated at 37° C. for 1.5 hours. Upon adding 30 ul of sterile water and 10 ul of 10×STE the reaction mixture was extracted with 100 ul of phenol/chloroform followed by a 100 ul chloroform extraction. cDNAs were collected via centrifugation after adding 200 ul of absolute ethanol (and overnight precipitation at −20° C.), dried and resuspended in 14 ul 1× STE to which 3.5 ul column loading dye was added.

The SEPHAROSE CL-2B matrix and STE buffer were equilibrated to room temperature, resuepended and used for casting a column in a 1-ml glass pipet.

After settling of the SEPHAROSE matrix, the column was washed with 10-15 ml of STE. The sample was loaded after which 3 ml of STE was added and 0.3 ml fractions were collected (monitoring the whole process with Geiger counter). The radioactivity in each fraction was estimated by measurement in a scintillation counter.

Analysis by Non-Denaturing Gel Electrophoresis 3 ml of 10×TBE, 5 ml of 30% acrylamide [(w/v), 29:1 of acrylamide:bis-acrylamide) and 22 ml of water were mixed, degassed, upon which 150 ul of 10% freshly made ammonium persulfate and 20 ul of TEMED were added. The solution was applied to the assembled gel moulds and left to settle. 8 ul of each fraction (collected from the column) that contained radioactivity was taken and mixed with 2 u of 5× loading buffer. Samples were loaded alongside a radioactive molecular weight marker and electrophorised. After electrophoresis, gels were fixed in 100 ml 7% acetic acid for 20-30 min, dried on Whatmann 3MM paper and exposed to X-ray film.

Processing the cDNA Fractions

Based on the results from the non-denaturing gel electrophoresis, fractions containing the desired size distribution were pooled. (Normally, fractions with cDNAs above 0.5 kb are collected. If desired, sub-libraries can be constructed by ligation of the selected different size fractions with the vector).

2 ul from the pooled fractions were removed and spotted on a Whatman GF/C filter. The filter was washed 3 times with 10 ml ice-cold TCA/pyrophosphate solution, rinsed with 10 ml of 70% ethanol, dried and counted with liquid scintillant to estimate the amount of cDNA present. Pooled fractions were precipitated overnight at −20° C. by adding 2 volumes of absolute ethanol and collected via centrifugation. Precipitation was assisted by adding purified tRNAs to 10 ug/ml as carriers. Upon washing, the pellet was air dried and resuspended in sterile TE or water to 10-20 ng/ul. The cDNAs were ligated to vector DNA with an excess at a molar ratio of 5:1. Subsequently, the ligation mixture was transformed to XL10-Gold bacterial cells (STRATAGENE) according the (corresponding) protocol.

EXAMPLE 1

1.1 Description and Construction of Expression Vector pGBFin2

1.1.a Rationale.

Expression screening in *A. niger* can be improved by a number of factors which when used in combination are likely to produce the most optimal result. An effective transformation system is preferred in order to obtain a sufficient number of fungal transformants. Care should be taken to keep the cDNAs in the library intact during the cloning procedure. Furthermore, screening will be most successful when expression levels of the gene product of the cDNA should be sufficiently high. Therefore, in the expression cloning constructs the functionalities used to drive expression of the cDNAs were derived from a gene which is highly expressed. In the integrative system the expression cassette is preferably directed to a locus which is highly expressed and which, even more preferably, has been amplified in the genome. In this example the glaA locus was chosen which is present in 3 copies in the genome of *A. niger* strain DS2978 (deposited 8 Apr. 1997 at the Centraalbureau voor Schimmelcultures, Baarn, The Netherlands under accession number CBS 646.97). Several expression vectors, designed both for efficient targeting to this locus and allowing different cDNA cloning strategies were constructed and tested (see examples 1-7).

1.1.b Basic Design of Integrative Expression Vectors.

Linear DNA molecules are preferred for targeted integration into the genome of filamentous fungi. Furthermore, both 5' and 3' ends (flankings) preferably consist of DNA homologous to the desired integration site. Transformation fragments, therefore, comprise the expression cassette (the gene of interest regulated by a suitable promoter and terminator) as well as a selection marker flanked by the 5' and 3' targeting domains. These fragments are cloned into an *E. coli* vector for propagation of the plasmid. The resulting expression vectors are designed such that *E. coli* sequences are removed during linearization and isolation of the transformation fragment.

For selection of transformants the amdS selection marker, expression of which is controlled by the *A. nidulans* gpdA promoter, is used. Using the strong gpdA promoter will predominantly result in one copy transformants.

To achieve high expression levels the cDNA is fused to the g/aA promoter. A Number of combinations of unique restriction sites for the (rare cutting) enzymes (e.g. PacI and AscI [Example 1], EcoRI and XhoI [Examples 4 and 6] or HindIII and XhoI [Example 7]) are introduced in a set of integrative expression vectors at the proposed transcription start point of the glaA promoter.

Since directed insertion (targeting) of rDNA molecules into the genome occurs through homologous recombination, rDNA cassettes is preferably flanked by DNA fragments homologous to the target site in the genome. Therefore the integration cassette is flanked at both the 5'- and the 3'-end by approximately 2 kb of DNA sequence homologous to the glaA locus. To facilitate the removal of the *E. coli* DNA from the construct, unique NotI sites were introduced (NotI restriction sites are rare, thus minimising the risk of unwanted digestion of the introduced cDNA).

1.1.c Construction of an Intermediate Expression Vector, pGBTOP8

Oligonucleotides AB5358 and AB5359 were annealed in equimolar amounts and ligated in the EcoRI and HindIII restriction sites of pTZ18R, thus introducing a NotI-XhoI-EcoRI-SnaBI-HindIII polylinker (the EcoRI site was not restored). The resulting plasmid was named pGBTOP1. A 1.8 kb XhoI-EcoRI fragment, comprising the promoter region of the glaA gene, was isolated from plasmid pAB6-1 (contains the entire *A. niger* glaA locus on a 15.5 kb HindIII fragment, cloned in pUC19 as is described in one of our previous patents, EP-A-0 635 574) and cloned in the XhoI-EcoRI sites of plasmid pGBTOP1, yielding plasmid pBG-TOP$_2$.

To mediate targeting of constructs to the 3' non-coding region of glaA two different parts of this region were cloned on either side of the expression cassette. These parts were designated 3' glaA and 3" glaA, the latter being the most downstream part of the region.

The 3" glaA fragment was generated by PCR using oligonucleotides AB5291 and AB5292 (oligo AB5291 was designed to disrupt an unwanted EcoRI site). The generated PCR fragment was used as a template in a second PCR reaction using oligonucleotides AB5361 and AB5292, thus generating a NotI site in the fragment. The PCR fragment was digested with NotI and XhoI and cloned in the corresponding restriction sites of plasmid pGBTOP2, yielding pGBTOP5.

Unwanted EcoRI sites in the 3' non-coding region of glaA were disrupted using a PCR approach. A fusion PCR reaction was carried out using oligo AB5288 (5'), AB5293 (3' reverse), AB5290 (internal, reverse) and AB5289 (internal, coding). Oligo s AB5290 and 5289 were complementary oligo s designed for disruption of the EcoRI site at that position while oligo AB5293 was designed to disrupt a second EcoRI site. The resulting fusion PCR product was digested with SnaBI and HindIII and cloned in the corresponding sites of pGBTOP2, resulting in pGBTOP6. pGBTOP6 was used as a template in a second PCR reaction using oligonucleotides AB5363 and AB5567. The resulting PCR product was digested with SnaBI and HindIII and cloned in the corresponding sites of pGBTOP5, resulting in plasmid pGBTOP8 (see FIG. 1).

1.1.d Construction of pGBFin2.

Using oligonucleotides 6963 and 7266, and 10 ng of vector pAB6-1 (EP-A-O 635 574) as a template, a P$_{glaA}$ specific PCR fragment was generated. This fragment was digested with EcoRI and SmaI and introduced in EcoRI and SnaBI digested vector pGBTOP-8, resulting in vector pGB-Fin1. The sequence of the introduced PCR fragment was confirmed by sequence analysis. XhoI sites were introduced to the P$_{gpdA}$-amdS fragment by PCR. Using oligonucleotides 7423 and 7424 and plasmid pGBAAS1 (EP-A-0 635 574) as a template a 3.1 kb fragment was generated. This fragment was digested with EcoRI and introduced in the EcoRI site of pTZ19R, resulting in plasmid pTZamdSX-1. The 2.6 kb XhoI-ClaI of pTZamdSX-1 was replaced by the corresponding fragment from plasmid pGBAAS-1 to avoid mutations caused by the PCR process. The 0.5 kb KpnI-ClaI of pTZamdSX-1 was replaced by the corresponding fragment from plasmid pTZamdSX-1 to avoid mutations caused by the PCR process. Sequence analysis of the remaining 0.5 kb fragment of the resulting plasmid pTZamdSX-2, revealed one single mutation in the P$_{gpdA}$ fragment.

The 3.1 kb XhoI fragment, comprising the P$_{gpdA}$-amdS selection cassette, was isolated from vector PTZamdSX-2 and introduced in the unique XhoI site of pGBFin1, resulting in vector pGBFin2 (see FIG. 2).

1.2 Expression of Phytase Using Expression Vector pGBFin2

1.2.a Rationale.

Both efficient targeting of the expression construct to the g/aA loci of *A. niger* DS2978 and a sufficiently high expression level of the cDNA of interest are preferred for optimal application of expression screening in *A. niger*. Therefore the properties of the expression construct were tested using a model gene, phyA, for which the expected protein production per gene-copy integrated at a glaA locus had been established previously.

1.2.b Construction of a Phytase Expression Vector, pGBFin5.

A phyA fragment was generated by PCR using oligonucleotides 6964 and 6965 and plasmid pAF2-2S (described in EP-A-0 420 358) as a template. The PCR fragment was cloned in the SmaI site of vector pTZ18R, resulting in pTZFyt1. Sequence analysis of the insert of pTZFyt1 revealed no deviations from the sequence present in pAF2-2S. A 1.7 kb Asci-PacI fragment comprising the complete phyA sequence, was isolated from pTZFyt1 and cloned in AscI-PacI digested pGBFin2, resulting in vector pGBFin5 (see FIG. 2).

1.2.c Transformation of *Aspergillus niger* DS2978 with pGBFin5.

Plasmid pGBFin5 (100 g) was digested with NotI (150 Units, 4 hours at 37° C.). Protein was removed by extraction with an equal volume Phenol-Chloroform-Isoamylalcohol (24:23:1). The DNA was concentrated by alcohol precipitation and used for transformation of *A. niger* DS2978 as described. Transformants were purified on selective minimal medium plates and subsequently stored.

1.2.d Analysis of pGBFin5 Transformants

Targeting of the integration cassette to the glaA locus was analysed for 24 independent transformants, using oligonucleotides 5454 and 5456, and for the presence of the phyA gene using the phyA specific oligonucleotides 6964 and 6965.

A PCR product indicative of correct targeting of the pGBFin5 integration cassette to a glaA locus was found in a high number of transformants (12 out of 24=50%), while all transformants showed a PCR product indicative for the presence of a phyA copy in their genome.

Six positive transformants were analysed for phytase production in a shake flask fermentation experiment. Phytase activity for all transformants was 140-180 U/ml. Such a production level is indicative for integration of one copy of pGBFin5 in each transformant.

It was concluded that both targeting frequencies and expression levels were sufficient for use of the designed expression system in expression cloning experiments.

EXAMPLE 2

2.1 Construction and Analysis of a cDNA Library 2.1.a Rationale.

Expression libraries are constructed from a pool of mRNA which is expected to comprise the transcripts of interest. For this reason it is preferable, though usually not necessary, to isolate mRNA from mycelium isolated from a culture grown under inducing conditions. The isolated mRNA is analysed for the presence of the transcript of interest and for the quality of the mRNA. If the mRNA is intact and comprises the transcript of interest it can be used for cDNA synthesis.

Cloning of the cDNA in the expression vector pGBFin2 requires the presence of a PacI site on the 5'- and of an AscI site on the 3'-end of the cDNA. Therefore the first strand priming oligonucleotide and the adapter sequences used were designed to meet these prerequisites. The adapter was designed in such a way that it is compatible with the PacI site in pGBFin2 whereas the PacI site is not restored after ligation of the cDNA in the vector. This makes discrimination between vector molecules comprising a cDNA insert and vector molecules without insert possible.

2.2 Preparation of a cDNA Library from *A. tubigensis*. mRNA Induced for Xylanase Activity.

*A. tubigensis* DS116813 (CBS323.90) was grown under inducing conditions. Medium samples were taken at different time points and analysed for xylanase activity. Maximum activity was reached after 66 hr culture, while xylanase activity levels remained constant till 7 days after start of the experiment. Mycelium samples were taken at different time points and total RNA was isolated from these samples. The presence of xylA specific transcripts was analysed in a Northern blot experiment using a xylanase specific probe. Maximum xylA mRNA levels were determined after 48 hours induction while xylA mRNA still was detectable after 66 hours. After prolonged incubation of the mycelium in inducing medium no xylA mRNA was detectable. In all cases the xylA specific transcript was apparently intact. From the total RNA isolated after 48 hr induction mRNA was isolated. After Northern analysis, showing that the xylA mRNA was intact, this mRNA was used for cDNA synthesis (according to the Superscript™ choice system [Gibco-BRL]) using oligonucleotide 6967 as a primer for first strand synthesis. After annealing of a PacI specific linker, the cDNA was digested with AscI and size separated using the Sephacryl columns supplied with the cDNA synthesis kit (Superscript™ choice system [Gibco-BRL]). Both mRNA and cDNA were analysed for the presence of intact xylA in the samples using Northern-respectively Southern blot analysis and by PCR analysis. The resulting cDNA was ligated in Asci-PacI digested pGBFin2 and introduced by electroporation into *E. coli* resulting in a primary library of approximately 17000 transformants. Analysis of 24 random colonies revealed 5 plasmids without insert, while the remaining plasmids had insert sizes between 0.5 and 2 kb. The *E. coli* library was pooled by scraping the plates in a total volume of 25 ml 2×TY medium. 10 ml medium was used to prepare glycerol stocks while 2×TY was added to the remaining *E. coli* suspension to a final volume of 100 ml. Plasmid DNA was isolated from this culture after 2 hours growth at 37° C.

EXAMPLE 3

3.1 Construction and Analysis of an Expression Library in *A. niger*

3.1.a Rationale

*A. niger* DS2978 is transformed using the DNA isolated from the cDNA library in *E. coli*, as described in Example 2.2 above. Transformants are selected for the presence of the amdS selection marker by growth on acetamide as the sole N-source. Since both the amdS selection marker and the cDNA expression cassette are present on the integrating fragment growth on acetamide is indicative for the presence of a cDNA expression cassette. Conidiospores of amdS positive transformants are transferred to selective medium plates to avoid isolation of false positives and are subsequently transferred to microtiter plates comprising solidified PDA slants. This master-library is used to screen for production of enzymes of interest, e.g. xylanase. Since it would be useful if enzyme producing transformants could be used directly for larger scale enzyme production it is of interest to determine enzyme-production levels in shake flask fermentations.

3.2 Transformation of *A. niger* DS2978.

DNA was isolated from the amplified *E. coli* cDNA library as described. Total plasmid DNA (100 g) was digested for 4 hours at 37° C. with NotI (150 U) to remove *E. coli* derived plasmid sequences and with PacI (30 U). After purification of the DNA by extraction with an equal volume of Phenol:Chloroform:Isoamylalcohol (24:23:1) the DNA was recovered by alcohol precipitation and dissolved in 100 l sterile demineralized water. Multiple *A. niger* DS2978 transformations were performed using $2.10^7$ protoplasts and 10 g of plasmid DNA. After approximately 10 days incubation at 30° C., 1900 transformants were picked and conidiospores were transferred to plates containing selective medium. After 3 days incubation at 30° C. conidiospores of each transformant were transferred to individual wells in a 96 well microtiter dish, each well containing approximately 100 l solidified PDA.

3.3 Analysis of the *A. niger* expression library. Conidiospores of individual transformants were transferred to xylanase detection plates made of *Aspergillus* minimal medium (per liter 6 g $NaNO_3$, 0.52 g KCl, 1.52 g $KH_2PO_4$, 1.12 ml 4 M KOH, 0.52 g $MgSO_4.7H_2O$, 22 mg $ZnSO_4.7H_2O$, 11 mg $H_3BO3$, 5 mg $FeSO_4.7H_2O$, 1.7 mg $CoCl_2.6H_2O$, 1.6 mg $CuSO_4.5H_2O$, 5 mg $MnCl_2.2H_2O$, 1.5 mg $Na_2MoO_4.2H_2O$, 50 mg EDTA, 10 g glucose) supplemented with 2% oat spelt xylan and 2% bacteriological agar #1 (Oxoid, England), which have a turbid appearance due to the presence of undissolved xylan. After 2 days incubation at 30° C. halo formation could be observed for 10 colonies, indicating degradation of xylan by xylanases. Conidiospores of positive transformants were isolated and used to inoculate PDA plates. DNA was isolated from single colonies and analysed by PCR for integration of the expression plasmid at the glaA locus ("targeting") using oligonucleotides 5454 and 5456.

8 out of 17 colonies were shown to be targeted to one of the g/aA loci (47%).

3.4 Analysis of Xylanase Production Levels in Transformants

Xylanase producing transformants, as identified in the xylanase plate assay, were grown in shake flask fermentation. Medium samples were taken after 5 days of fermentation and analysed for xylanase activity. Results are presented in Table I.

3.5 Genetic Analysis of Xylanase Producing Strains 3.5.a Rationale.

Multiple xylanase encoding genes have been found in fungi. Therefore it was of interest to determine if each xylanase producing strain identified in the expression cloning experiment contains an identical cDNA. Furthermore, clear differences were found between individual xylanase producing strains. These differences could be caused both by the presence of different xylanase encoding genes or by differences in the 5'-non coding region of the cDNA. The latter could be due to partial degradation of mRNA during the RNA or mRNA isolation procedure or due to incomplete cDNA synthesis. To investigate this the 5'-sequences of the introduced cDNAs were determined.

3.5.b Analysis Xylanase Producing Clones.

PCR templates were prepared for each xylanase producing transformant as described. Transformants were analysed for the presence of an expression construct comprising xylA cDNA in a PCR experiment using oligonucleotides 6856 (xylA internal) and 6963 ($P_{glaA}$). Transformants #5C2 and #7A8 were shown to comprise an expression cassette with the xylA gene fused to the $P_{glaA}$.

Using oligonucleotides 6963 ($P_{glaA}$ specific) and 6967 (3' end cDNA specific) PCR fragments were generated which were expected to comprise the entire cDNA as well as 200 bp of $P_{glaA}$. A partial DNA sequence of the PCR fragments was determined using oligonucleotide 6963 for six transformants. Sequences indicative of the presence of both the xylA gene (2 clones) and of the xylB (4 clones) were detected (xylA and xylB DNA sequences are described in our previous patent applications EP-A-0 463 706 and WO 94/14965, respectively). Different lengths of the 5'-non translated region were found. However, no relation could be observed between the length of the 5'-non translated region of the cDNA and the xylanase production levels of different xylB transformants. In contrast, the short 5'-non translated region found in the xylA positive transformant #5C2 resulted in a significant reduction of XYLA activity. However, it is clear that production levels were still sufficient to identify this transformant in a plate assay.

Table I. Analysis of xylanase producing transformants. Positive transformants were analysed for xylanase production levels in a fermentation experiment. The identity of the xylanase encoding genes was determined by partial sequencing of the cDNA insert. Details are described in the text.

TABLE I

| Transformant | EXU/ml | Gene | Sequence | SEQ ID NO: | remarks |
|---|---|---|---|---|---|
| DS2978 | 3 | — | | | Parent strain |
| #2G1 | 64 | xylB | cctcaagc-caagtctctt tcaacATG | SEQ ID NO:23 | |
| #3A11 | 290 | xylB | gtctctttcaac ATG | SEQ ID NO:24 | |
| #3A12 | 27 | nd | | | |
| #4C10 | 401 | xylB | ctcctcaagc-caagtct ctttcaacATG | SEQ ID NO:25 | |
| #5C2 | 37 | xylA | atcatcATG | SEQ ID NO:26 | |
| #5C12 | 2 | — | | | Negative in plate assay |
| #7A8 | 505 | xylA | aaaagccctt-tactactt catacatcaat-catc ATG | SEQ ID NO:27 | |
| #7B4 | 51 | nd | | | |
| #11E3 | 272 | xylB | ctcaagc-caagtctcttt caacATG | SEQ ID NO:28 | |

TABLE I-continued

| Transformant | EXU/ml | Gene | Sequence | SEQ ID NO: | remarks |
|---|---|---|---|---|---|
| #14B1 | 43 | nd | | | |
| #14B5 | 52 | nd | | | | nd = not determined

EXAMPLE 4

4.1 Construction and Analysis of an Integrative Expression Vector Applicable for EcORI-XhoI-Mediated cDNA Cloning (pGBFIN11).

4.1.a Rationale

Expression libraries are constructed from pools of cDNA. The cDNA encoding the desired activity is screened for (detected) via a screening format described previously. Since the exact characteristics of the cDNA (for example the restriction enzyme sites present within the cDNA) in most cases are not known before actual identification the absence of restriction sites in the cDNA. Therefore, the possibility exists that in the construction as described in example 2 the desired cDNA still contains an internal AscI site and thus will be cloned as a non-full length inactive clone which cannot be screened for.

As a consequence plasmid pGBFIN11 has been constructed which allows cloning of cDNAs with EcoRI-XhoI cohesive ends without avoiding the danger of internal restriction sites. The 3' primer used for first strand cDNA synthesis contains a (non-methylated) XhoI site whereas during the synthesis of cDNA methylated dCTPs are used. As a consequence the cDNAs can be digested with XhoI avoiding the fragmentation of cDNAs because of internal XhoI sites (these XhoI sites are methylated and thus not digested). pGBFIN11 is a pGBFIN2 derived vector in which the existing XhoI and EcoRI sites have been removed upon which the cDNA cloning site has been changed from PacI-AscI into EcoRI-XhoI. Thus, all features and functionalities in the expression vector are identical except of the restriction sites used for cloning the cDNAs.

4.1.b Construction of the pGBFIN11 Vector

In a first step the existing XhoI, HindIII, ScaI and EcoRI present at the 5' end of the gpdA promoter were removed via PCR and a (rare) cutter site SnaBI was introduced, resulting in intermediate construct pGBFIN12. In a second PCR step the existing glaA promoter and cDNA cloning site were adjusted in such a way that the 1) existing PacI-AscI cDNA cloning site was changed into a EcoRI-XhoI cloning site, II) at the same time the EcoRI site in the promoter was inactivated, III) at the same time the promoter was shortened (starting from the SaA site at position 6084 in pGBFIN2 instead of starting from the XhoI site at position 5289 in pGBFIN2) and IV) at the same time the XhoI site present at position 5289 was inactivated and a (second) rare cutter restriction enzyme was introduced. The resulting plasmid (pGBFIN11) is depicted in FIG. 3.

4.2 Expression of Phytase Using Vector pGBFIN11

4.2.a Rationale

In the pGBFIN11 vector a test gene has been inserted (e.g. phytase) in a similar fashion as has been described in example 1.2 for the pGBFIN2 vector. The resulting vector, pGBFIN13, has been tested alongside the pGBFIN5 vector to demonstrate the functionality of this pGBFIN11-type vector.

4.2.b Construction of a Phytase Expression Vector, pGBFIN13

Similar to the situation described for the pGBFIN2 vector (example 1; 1.2.b), also the functionality of the pGBFIN11 vector was tested via the use of a model gene, phyA.

4.2.c Transformation of *Aspergillus niger* with pGBFIN13

Similar to the situation described for the pGBFIN2 vector (example 1: 1.2.c) the pGBFIN13 vector was digested with NotI in order to generate the linear fragment which could be used for targetting during transformation. After transformation, randomly selected transformants were purified in order to allow subsequent analysis.

4.2.d Analysis of the pGBFIN13 Transformants

Again, similar to the situation described for the pGBFIN2 vector (example 1: 1.2.d) the purified pGBFIN13 transformants were tested for targetting of the constructs at the correct locus and for expression of phytase. Both targetting frequencies and expression of the phytase were in the range of what has been described previously for the pGBFIN2 transformants. Thus, it was concluded that for the pGBFIN11 vector both the targetting frequencies and the expression levels were sufficient for use of the designed expression system in expression cloning of cDNAs with EcoRI-XhoI cohesive ends.

EXAMPLE 5

5.1.a Rationale

Upon demonstration of the functionality of the pGBFIN11 vector the complete expression cloning system based on this type of vector (EcoRI-XhoI cohesive ends) was tested. Since the introduction of an EcoRI-XhoI cDNA cloning site allowed the use of the STRATAGENE cDNA cloning kit, the applicability of this system (which has the benefit of avoiding the digestion of the intact cDNAs during restriction digest to generate the 3'cohesive cloning site) in combination with the new pGBFIN11 vector was tested. Similar to what has been described in examples 2 and 3, an *A. niger* derived pool of RNA was used to generate, with the STRATEGENE protocol optimized for cloning in pGBFIN vectors as has been detailed in material and methods, a pool of cDNAs (with EcoRI-XhoI cohesive ends). This pool of cDNAs was cloned into the pGBFIN11 vector to generate an *E. coli* library. Subsequently, cloning efficiencies were compared with the previous library construction in the pGBFIN2 vector.

5.1.b. Preparation of a cDNA Library from a for Xylanases Induced *Aspergillus* Culture.

Mycelium from which (as has been described previously) was known that xylanases were expressed at the time of harvesting was used to substract total RNA as has-been detailed in Material and Methods. Subsequently, the total RNA pool was further purified by centrifugation through a CsCl cushion. Upon checking quality of the RNA, mRNA was isolated via a modified protocol with the Pharmacia purification Kit. For cDNA synthesis the Strategene cDNA Synthesis KIT was used. The corresponding cDNA synthesis protocoll was adapted towards optimization of cloning into the pGBFin vectors. Main adaptions included; 1) Amounts of cDNA were quantified via precipitation by TCA; 2) Phosphorylation of the ends of the cDNAs was omitted and cDNAs were ligated to vector DNA which was not dephosphorylated. This prevented the ligation of multiple inserts into one vector (which would prevent the expression of several if not all inserts present in that vector). 3) The cDNA was extracted with phenol/chloroform after digestion with XhoI rather than after size fractionation. 4) Both MMLV-RT and Thermoscript were used in the first strand synthesis which resulted in cDNAs with longer lengths than the use of either of the enzymes alone. 5) Control reactions were traced with [alpha$^{32}$P]DATP (800 Ci/mmol, in order to prevent interference with synthesis) for quality control. A pool of cDNAs was constructed constructed according the thus modified protocoll.

For the pGBFin11, a pool of well double-digested (EcoRI-XhoI) pGBFin11 vector (background ligation <1%) was prepared. The generated cDNA pool was ligated into the pGBFin11 vector and transformed to *E. coli* XL10-Gold bacterial cells to generate a library.

5.1.c. Analysis of the *E. coli* cDNA Library (in the pGBFin11 Vector)

The procedure described thusfar in this example resulted in a significant increase in the efficiency of ligation and transformation. With the pool of cDNA isolated according to the optimized procedure it was possible to obtain in combination with the well double-digested pGBFin11 vector-pool to obtaine an *E. coli* library of a size of $10^6$-$10^7$ starting from 1 ug of pGBFin11.

Next, via hybridisation experiments the frequency of gpdA and xylB cDNAs in the *E. coli* cDNA library were established. Since the gpdA gene represents a relatively long gene and the xylB gene is relatively short, the comparison of percentages full length clones could clarify the quality of the generated cDNAs and identify whether there were differences in the efficiency of generating full length cDNAs between short en longer mRNAs.

Upon identification of positive xylB and gpdA clones, a selected number was sequenced to determine the persentage of full length clones within cDNA population originating from these particular genes. Both for the gpdA and xylB cDNAs it was shown that the percentage of full length clones was above 85%. Furthermore, the sequencing showed that none of the clones contained multiple inserts.

Thus, it was concluded that the optimized RNA purification, cDNA synthesis and cloning protocoll resulted in a considerably improved efficiency and quality of cDNA library construction (in terms of size and frequencies of the libraries, in terms of percentages full length and in terms of cloning only one cDNA insert in the expression vector)

5.1.d. Transformation of xylB Containing pGBFin11 Constructs to *A. niger* and Screening for Xylanase Activity A number of the xylB clones identified (and analysed in 5.1.c) were transformed to *A. niger* (similar as has been described for the pGBFin5 and pGBFin13 vectors). After purification of a selected number of transformants these transformants were screened on plate for xylanase activity. All transformants tested were positive in the xylanase plate assay, demonstrating the applicability of the pGBFin11 vector for expression cloning purposes in *A. niger*.

EXAMPLE 6

6.1 Construction of a Second Integrative Expression Vector Applicable for EcoRI-XhoI Mediated cDNA Cloning (pGBFin22)

6.1.a Rationale

During the construction of the pGBFin11 vector the second PCR fragment (used to inactivate the EcoRI site in the glucoamylase promoter, amongst the other modifications listed in example 4) was sequenced to prove correct modification. This demonstrated the correct modification of the indicated restriction sites but also showed a number of small PCR errors in the more upstream parts of the glucoamylase promoter. Therefore based on the non-changed glycoamylase promoter region in pGBFin12 a new vector was constructed in which the introduced PCR errors were absent and which was suitable for cloning of cDNAs with EcoRI-XhoI cohesive ends.

6.1.b Construction of Expression Vector pGBFin22

In pGBFin12 (FIG. 3) the remaining XhoI site was inactivated after XhoI digestion via end-filling with $T_4$ DNA polymerase and backligation which resulted in pGBFin17 (see FIG. 6). In pGBFin17 the remaining EcoRI site was removed similarly (EcoRI digestion followed by $T_4$ DNA polymerase end-filling and backligation) which resulted in plasmid pGBFin18 (see FIG. 7). Two primers containing a EcoRI and XhoI restriction sites and (upon annealing together) containing cohesive ends to PacI and AscI were annealed. Primers were constructed in such a way that upon cloning the annealed primers into PacI- and AscI-digested pGBFin18 no (extra) ATG was generated at the cloning site of the cDNAs. Thus, by cloning of the described annealed primers in the PacI- and AscI-digested pGBFin18 a cloning site for cDNAs with EcoRI-XhoI cohesive ends was generated. The thus obtained plasmid was named pGBFin22 (see FIG. 8).

6.2 Expression of Phytase Using Vector pGBFin22

6.2.a Rationale

In the pGBFin22 vector a test gene has been inserted (e.g. phytase) in a similar fashion as has been described in example 4 for the pGBFin11 vector. The resulting vector, pGBFin25, has been tested for phytase production to its functionality.

6.2.b Construction of a Phytase Expression Vector, pGBFin25 pGBFin13 was digested with EcoRI to liberate the phytase gene. This phytase encoding EcoRI gene fragment was cloned into pGBFin22. Upon identification of a clone with the correct orientation of the phytase gene, this clone was designated pGBFin25.

6.2.c Transformation of *A. niger* with pGBFin25 and Analysis of pGBFin25 Transformants pGBFin25 was used for transformation to *A. niger* and subsequent analysis of transformants as has been detailed in examples 1 and 4 for the pGBFin5 and pGBFin13 transformants respectively. Results were similar as has been indicated for the pGBFin13 transformants which demonstrated the applicability of the pGBFin22 vector for expression cloning purposes.

EXAMPLE 7

7.1 Construction Integrative Expression Vector Applicable for HindIII-XhoI Mediated cDNA cloning, pGBFin23

7.1.a Rationale

Upon obtaining the set of integrative expression cloning vectors described thusfar it was recognised that the availability of an expression cloning vector which could be used for cloning cDNAs with HindIII 5' cohesive ends could be usefull. Both in terms of being able to use cDNA pools which were already constructed for other purposes with HindIII-XhoI cohesive ends and because of the fact that in this approach no changes had to be made to the glucoamylase promoter.

7.1.b Construction of a Phytase Expression Vector Applicable for HindIII-XhoI Mediated cDNA Cloning, pGBFIN23

In pGBFin17 the remaining HindIII site was removed (HindIII digestion followed by $T_4$ DNA polymerase end-filling and backligation) which resulted in plasmid pGBFin19 (see FIG. 9). Two primers containing a HindIII and XhoI restriction sites and (upon annealing together) containing cohesive ends to PacI and AscI were annealed. Primers were constructed in such a way that upon cloning the annealed primers into PacI- and AscI-digested pGBFin19 no (extra) ATG was generated at the cloning site of the cDNAs. Thus, by cloning of the described annealed primers in the PacI- and AscI-digested pGBFin19 a cloning site for cDNAs with HindIII-XhoI cohesive ends was generated. The thus obtained plasmid was named pGBFin23 (see FIG. 10).

7.2 Expression of Phytase Using Vector pGBFin23

7.2.a Rationale

In the pGBFin23 vector a test gene has been inserted (e.g. phytase) in a similar fashion as has been described in example 4 for the pGBFin11 vector. The resulting vector, pGBFin26, has been tested for phytase production to demonstrate its functionality.

7.2.b Construction of a Phytase Expression Vector, pGBFin26

In this example the phytase gene was PCRed with a 5'oligo which contained a HindIII site and a 3'oligo containing an XhoI site. Upon digestion with HindIII and XhoI this fragment was cloned directly into pGBFin23, thus generating pGBFin26. Upon isolation of a number of clones which contained the phytase gene, the phytase inserts were sequenced in order to check for the introduction of putative PCR errors. Finally, of a correct pGBFin26 plasmid (no changes in the encoded protein sequence) was selected and used for transformation and subsequent analysis.

7.2.c Transformation of *A. niger* with pGBFin26 and Analysis of pGBFin26 Transformants pGBFin26 was used for transformation to *A. niger* and subsequent analysis of transformants as has been detailed in examples 1, 4 and 6 for the pGBFin5, pGBFin13 and pGBFin25 transformants, respectively. Results were similar as has been indicated for the pGBFin13 transformants which demonstrated the applicability of the pGBFin23 vector for expression cloning purposes.

EXAMPLE 8

8.1 Construction of AMA1-Based Plasmid Expression Vectors Suitable for cDNA Expression Cloning (pGBFin6 and pGBFin15)

8.1.a Rationale

In another example the functionalities to drive high expression of the cloned cDNAs and a selectable marker were used in plasmids which contain in addition a so-called AMA1 sequence. As a results an expression cloning plasmid was generated which was autonomously maintained in

*Aspergillus*. In this type of expression cloning vectors the highly efficient transformation frequencies obtainable with AMA1-type based vectors and the functionalities which drive high espression of the cloned cDNAs are combined. Two expression vectors which differed in the selection marker gene used for selection of transformants in *Aspergillus* and both designed for AMA1-based expression cloning systems were constructed 8.1.b Construction of the pGBFin6 Vector pTZamdSX-2 (see FIG. 2) was linearised with HindIII upon which the 5.2 kb HindIII AMA1 fragment from *A. nidulans* (as described by Aleksenko and Clutterbuck, 1998) was cloned into it, resulting in intermediate plasmid pAMAamdS. Next pAMAamdS was digested with KnpI and BglII and the approx. 9 kb AMA1 containing fragment was isolated. Upon digestion of the pGBFin2 vector (see FIG. 2) with KnpI and BglII the 5.2 kb glucoamylase promoter containing fragment was isolated. The 5.2 kb fragment derived from pGBFin2 is cloned into the 9 kb fragment from pAMAamdS resulting in AMA1- and aceetamide-selection-based expression cloning plasmid pGBFin6 (See FIG. 11).

8.1.b Construction of the pGBFin15 Vector pGBFin6 was digested with XhoI and the glucoamylase promoter containing fragment was isolated. Next, the pAN8-1 plasmid (see FIG. 12), containing functional ble gene (encoding phleomycin resistance) driven by a *A. nidulans* gpdA promoter and terminated by the trpC terminator was used as a template in a PCR reaction. PCR primers were designed in such a way that a fragment was generated containing a truncated (but still completely functional) gpdA promoter, the ble gene and a truncated (but still completely functional) trpC terminator which contained in addition at both ends of the fragment a functional XhoI site. Furthermore, the 5'primer contained a HindIII site which was necessary for further cloning steps (as detailed in the construction of pGBFin15). Upon XhoI digestion of the approx. 1.9 kb PCR product it was cloned into the XhoI fragment isolated previously from pGBFin2. The resulting plasmid (pGBFin14; see FIG. 13) was checked for the correct orientation via restriction analysis and for PCR errors via sequencing. pGBFin14 was linearised with HindIII upon which the 5.2 kb AMAL HindIII fragment was inserted, resulting in plasmid pGBFin15 (see FIG. 14).

8.2 Expression of Phytase in AMA1-Based Vectors 8.2.a Rationale

The AMA1-based expression constructs were tested for the expression of a phytase similarly as has been described for the integrative expression vectors. Again a test gene was inserted (e.g. phytase) in a similar fashion as has been described in example 1 for the pGBFin5 vector. The resulting vectors, were tested for phytase production to demonstrate the functionality and applicability of AMA1-based expression vectors 8.2.b Construction of pGBFin7 and pGBFin16

Both the pGBFin6 and the pGBFin15 vectors linearised via double digestion with PacI and AscI. Next the pGBFin5 plasmid was digested with PacI and AscI to liberate the phytase gene encoding fragment (with PacI and AscI cohesive ends). This phytase fragment was cloned directly into the digested pGBFin6 and pGBFin15 vectors to generate, pGBFin7 and pGBFin16, respectively.

8.2.c Transformation of *Aspergillis niger* with pGBFin7 and pGBFin16 pGBFin7 and pGBFin16 were transformed to *A. niger* according the procedures described in previous examples and further detailed in Material and Methods. The pGBFin7 transformants were selected on media containing aceetamide as sole nitrogen source, whereas the pGBFin16 transformants were selected on media containing phleomycin. Both plasmids demonstrated a significantly increased transformation frequency compared to the integrative type of expression vectors; transformation frequencies of AMA1-based plasmids were up to $10^5$ transformants per ug of plasmid.

Positive transformants were purified by re-streaking for single colonies on selective medium and finally stored.

8.2.d Analysis of Phytase Expression in pGBFin16 Transformants

After purification 20 randomly selected pGBFin16 transformants were fermented in shake flasks using the same medium (in this case supplemented with phleomycin) as has been described for the integrative vectors. Fermentation samples were assayed for phytase production which was demonstrated to range in all cases (except for one) from approx. 40 U/ml to 60 U/ml. In one particular case the expression was 117 U/ml which was probably a result of integration of the pGBFin16 plasmid into the genome (see also comments in example 1; 1.2.d.)

These results demonstrate that AMA1-based plasmids as described in this example can be used for direct expression cloning in *Aspergillus*. Due to the use of the glaA functionalities which are capable of driven high level expression of cloned cDNAs production, although reduced compared to the expression after integration at a high expression locus, the expression is still certainly high enough for efficient screening in a AMA1-containing expression library, especially when the significantly increased transformation frequency is taken into account. A further advantage of the AMA1-based vectors is provided by the fact that recovery (re-isolation) of these plasmids from the filamentous fungal expression host is simplified compared to integrative plasmids. Direct transformation of *E. coli* with total DNA isolated from the host in question will suffice in this respect.

The invention claimed is:

1. A method for isolating a DNA sequence coding for a desired protein, said method comprising the steps of:
   (a) preparing, in a suitable cloning vector comprising a selection marker gene, a DNA library from an organism suspected of being capable of producing one or more desired proteins,
   (b) transforming filamentous fungal host cells with the DNA library,
   (c) culturing the transformed host cells obtained in (b) under conditions conducive to the expression of DNA sequences in the DNA library, and
   (d) screening for clones of the transformed host cells expressing a desired protein by analysis of the proteins produced in (c) wherein the DNA sequence expressed in (c) does not complement the selection marker gene.

2. The method according to claim 1, wherein the cloning vector comprises a DNA fragment which is homologous to a DNA sequence in a predetermined target locus in the genome of the filamentous fungal host cell.

3. The method according to claim 2, wherein the predetermined target locus comprises a highly expressed gene.

4. The method according to claim 2, wherein the filamentous fungal host cell comprises more than one copy of the predetermined target locus.

5. The method according to claim 1, wherein the cloning vector is a vector which is capable of autonomous maintenance in a filamentous fungal host cell.

6. The method according to claim 5, wherein the vector capable of autonomous maintenance is a vector comprising the AMA1-sequence of the species *Aspergillus nidulans*.

7. The method according to claim 1, wherein the DNA sequence coding for the desired protein is operably linked to a promoter from a highly expressed filamentous fungal gene.

8. The method according to claim 1, wherein the filamentous fungal host cell is a species of the genera *Aspergillus* or *Trichoderma*.

9. The method according to claim 1, wherein the filamentous fungal host cell is a species selected from the group consisting of *Aspergillus nidulans, Aspergillus otyzae, Aspergillus sojae, Aspergillus niger* and *Trichoderma reesei*.

10. The method according to claim 1, wherein the organism suspected of being capable of producing one or more desired proteins is a eukaryote.

11. The method according to claim 10, wherein the eukaryote is a fungus.

12. A method according to claim 1, wherein the desired protein is an enzyme.

13. The method according to claim 10, wherein the eukaryote is a filamentous fungus.

* * * * *